(12) United States Patent
Eklund

(10) Patent No.: US 8,519,165 B2
(45) Date of Patent: Aug. 27, 2013

(54) PROCESS FOR PREPARING BENZOFURANS

(75) Inventor: Lars Eklund, Karlskoga (SE)

(73) Assignee: Cambrex Karlskoga AB, Karlskoga (SE)

( * ) Notice: Subject to any disclaimer, the term of this patent is extended or adjusted under 35 U.S.C. 154(b) by 151 days.

(21) Appl. No.: 12/681,299

(22) PCT Filed: Oct. 2, 2008

(86) PCT No.: PCT/GB2008/003341
§ 371 (c)(1),
(2), (4) Date: Jul. 28, 2010

(87) PCT Pub. No.: WO2009/044143
PCT Pub. Date: Apr. 9, 2009

(65) Prior Publication Data
US 2010/0292319 A1    Nov. 18, 2010

(30) Foreign Application Priority Data

Oct. 2, 2007  (GB) .................................. 0719180.2

(51) Int. Cl.
*C07D 307/80* (2006.01)
(52) U.S. Cl.
USPC ....................................................... 549/467
(58) Field of Classification Search
USPC ....................................................... 549/467
See application file for complete search history.

(56) References Cited

U.S. PATENT DOCUMENTS

| | | | |
|---|---|---|---|
| 3,340,300 | A | 9/1967 | Safir et al. |
| 3,364,210 | A | 1/1968 | Safir et al. |
| 3,558,667 | A | 1/1971 | Mooradiam |
| 5,223,510 | A | 6/1993 | Gubin et al. |
| 5,684,200 | A | 11/1997 | Harreus et al. |
| 5,854,282 | A | 12/1998 | Mellin |
| 6,844,470 | B2 | 1/2005 | Frater et al. |
| 6,846,936 | B2 | 1/2005 | Biard |
| 2001/0012900 | A1 | 8/2001 | Schouteeten et al. |
| 2004/0010032 | A1 | 1/2004 | Biard |
| 2004/0044070 | A1 | 3/2004 | Bourriague-Seve et al. |
| 2004/0048921 | A1 | 3/2004 | Fino et al. |
| 2005/0049302 | A1 | 3/2005 | Gutman et al. |

FOREIGN PATENT DOCUMENTS

| | | |
|---|---|---|
| BE | 670495 | 4/1966 |
| EP | 0270342 A | 6/1988 |
| GB | 1049086 | 11/1966 |
| JP | 60169446 | 9/1985 |
| JP | 2002371076 A | 12/2002 |
| WO | 2007/140989 A2 | 12/2007 |
| WO | 2009044143 | 4/2009 |
| WO | 2010038029 | 4/2010 |

OTHER PUBLICATIONS

Simon et al., Chemical Abstracts, 1974.

Takeda N et al: "Efficient synthesis of benzofurans utilizing [3,3]-sigmatropic rearrangement triggered. by N-trifluoroacetylation of oxime ethers: short synthesis of natural 2-arylbenzofurans" European Journal of Organic Chemistry, vol. 9, Jan. 25, 2007, pp. 1491-1509.
Sheradsky T: "Application of the Fischer indole synthesis to the preparation of benzofurans" Tetrahedron Letters, vol. 43, 1966, pp. 5225-5227.
Miyata et al: "Efficient [3,3]-sigmatropic rearrangement accelerated by a trifluoroacetyl group: Synthesis of benzofurans under mild conditions" Organic Biomolecular Chemistry, vol. 1, 2003, pp. 254-256.
Grandberg I I et al: "Indoles. XXIV. O-Phenylhydroxylamine as the 0-analog of phenylhydrazine in the Fischer reaction" Chemistry of Heterocyclic Compounds (A Translation of Khimiyageterotsiklicheskikh Soedinenii), Plenum Press Co., New York, NY, US, vol. 1, No. 1, Jan. 1, 1973, pp. 31-36.
Vorob'Ev S S et al: "Intramolecular cyclization of 0-(3,5-dinitrophenyl) and 0-(3-amino-5-nitrophenyl) ketoximes, products of transformations of 1,3,5-trinitrobenzene. The synthesis of nitrobenzo[b]furans and 4-hydroxynitroindoles" Russian Chemical Bulletin, Kluwer Academic Publishers-Plenum Publishers, NE, vol. 56, No. 5, May 1, 2007, pp. 1020-1027.
Vazzana I et al: "7-(substituted amino)-2,3-polymethylenebenzofuran derivatives with tracheal relaxant activity" FARMACO, Societa Chimica Italiana, Pavia, IT, vol. 51, No. 10, Jan. 1, 1996, pp. 637-642.
Castellino A et al: "Synthesis of benzofurans from oxygenated phenoxyamines" Journal of Organic Chemistry, vol. 49, No. 23, 1984, pp. 4399-4404.

(Continued)

*Primary Examiner* — Taofiq A Solola
(74) *Attorney, Agent, or Firm* — Banner & Witcoff, Ltd.

(57) ABSTRACT

There is provided a process for the preparation of a compound of formula (I), wherein $R^1$, $R^2$, $R^3$, $R^4$, X and Y are as described in the description. Such compounds may, for example, be useful intermediates in the synthesis of drugs such as Dronedarone. Intermediate steps of the process comprise formulae according to (II) and (III).

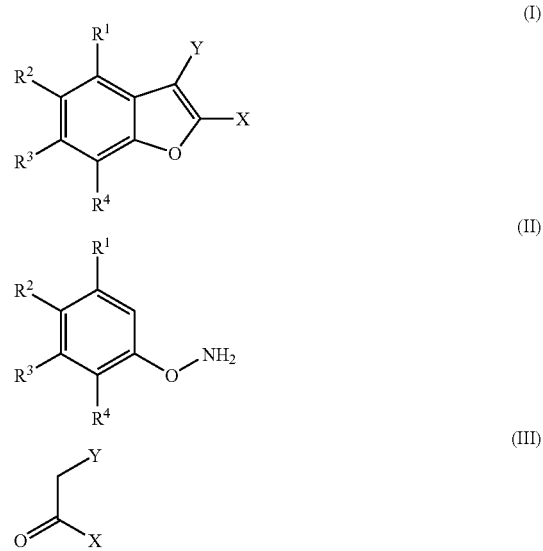

23 Claims, No Drawings

(56) References Cited

OTHER PUBLICATIONS

Dell et al: "Product class: 1 benzo[b]furans" Science of Synthesis—Houben-Weyl Methods of Molecular Transformations : Category 4 : Compounds With Two Carbon-Heteroatom Bonds, vol. 10, Jan. 1, 2001, pp. 11-86.
Alemagna Andreina et al: "Aromatic nucleophilic substitution on chromium tricarbonyl-complexed haloarenes: a new synthesis of 0-aryloximes and their cyclization to benzofurans" Journal of the Chemical Society, Chemical Communications, Chemical Society. Letchworth, GB, Jan. 1, 1985, pp. 417-418.
International Search Report for PCT/GB2008/003341 (WO2009/044143 A4), Issued Feb. 16, 2009.
Lim et al., Organic Letters, 2007, vol. 9, No. 21, 4139-4142.
Intention to Grant EP 08806486.
cation Claims intended for grant EP 08806486.
Decision to Grant EP 08806486.
Alemagna A., et al., "Nucleophile Aromatic Substitution of Tricarbonyichromium-complexed Haloarenes: Synthesis of O-Aryloximes and Their Cyclization to Benzofurans," Synthesis, (1987), 2, 192-196.
Ares J., et al., "Synthesis and Biological Evaluation of Flavonoids and Related Compounds as Gastroprotective Agents," Bioorganic and Medicinal Chemistry Letters, (1996), 6(8), 995-998.
Blake J. A. et al., J. Org. Chem., (2004) 69(9), 3112-3120.
Boyle P. H. et al., ARKIVOC, 2003 (vii) 67-79.
CAPLUS record No. 1992:426336 (1992).
CAPLUS record No. 1962:404727 (1962).
CAPLUS record No. 1970:516689 (1970).
Dutov M. et al., "Synthesis of 4,6-dinitrobenzo[b]furans from 1,3,5-trinitrobenzene," Mendeleev Communications, (2005) 5, 202-204.
El-Ansary, A.K. et al., "Synthesis and Screening for Analgesic Activity of Certain 1,3-Diketone Derivatives," Egyptian Journal of Pharmaceutical Sciences (1991), 32(3-4), 709-17.
Endo et al. (1982), "Acid-Catalyzed Solvolysis of N-Sulfonyl-and N-Acyl-0-arylhydroxylamines. Phenoxenium Ions", J. Am. Chem. Soc, 104; 6393-6397.
International Search Report for PCT/GB2009/002346, mailed Jan. 15, 2010.
Heilbron et al., J. Chem. Soc., (1934) 1581 (abstract).
International Search Report for PCT/GB2008/003341, mailed May 6, 2009.
Jones et al., Makromolekulare Chemie (1961), 50, p. 232-43.
Jones et al., Journal of Chem. Soc., Perkin Trans 2 (1975), 11, p. 1231-4.
Jones et al., J. Chem. Soc., (1949) 562-565 (abstract).
Makhova N. N. et al., Izvestiya Akademii Nauk SSSR, Seriya Khimicheskaya, (1982), 9, 2107-2110.
Patent Chemistry Database extract XP-002560090 (2003).
Santos, Synlett, (2005), 20, 3095-3098 (abstract).
Sheradsky T., et al., Bio-Organic Chemistry, (1980) 12, 2781-2786.
Sheradsky et al (1972), "Introduction of the Aminnooxy Group on to Nitroaromatic and Heterocyclic Rings: Synthesis and Properties of O-(Nitroaryl) Hydroxylamines", Tetrahedron, 28; 3833-3843.
Sheradsky, T., "O-(2,4-Dinitrophenyl) Oximes. Synthesis and Cyclization to 5,7-Dinitrobenzofurans," Sep. 1967.
Search Report in App. No. GB0719180.2 dated Apr. 14, 2008.
Wasylenko W. A. et al., "Generation of Oxynitrenes and Confirmation of Their Triplet Ground States," J. Am. Chem. Soc., (2006) 128(40), 13142-13150.
Castellino et al., "Synthesis of Phenoxyamines," J. Org. Chem., vol. 49, No. 8, p. 1348-1352, 1984.
Sheradsky, Tuvia, "O-(2,4-Dinitrophenyl) Oximes. Synthesis and Cyclization to 5,7-Dinitrobenzofurans," Sep. 1967.

PROCESS FOR PREPARING BENZOFURANS

The present invention relates to a process for the manufacture of various benzofurans by reaction of an arylhydroxylamine and a ketone, and the use of such benzofurans in the synthesis of compounds, e.g. drugs, containing such cores, for instance anti-arrhythmia drugs such as Dronedarone (N-{2-(n-butyl)-3-[4-(3-dibutylamino-propoxy)-benzoyl]-benzofuran-5-yl}methane-sulfonamide).

Dronedarone is a Class III anti-arrhythmia drug for the prevention of cardiac arrhythmias such as atrial fibrillation (AF). AF is a condition characterised by an irregular heart beat and occurs when the atria (the upper chambers of the heart) contract very rapidly. This causes the lower chambers of the heart, the ventricles, to contract chaotically so that blood is inefficiently pumped to the body which can lead to tissue damage and even death.

Dronedarone is prepared via a stepwise procedure which involves the synthesis of a number of intermediates, including 2-butyl-3-(4-methoxybenzoyl)-5-nitrobenzofuran and 2-butyl-3-(4-hydroxybenzoyl)-5-nitrobenzofuran.

2-Butyl-3-aroyl-5-nitrobenzofurans are typically synthesised via Friedel-Craft acylation of 3-unsubstituted 2-butyl-5-nitrobenzofurans. Such reactions are described in U.S. Pat. No. 5,223,510 and U.S. Pat. No. 5,854,282, Japanese patent document JP 2002-371076 and international patent application WO 2007/140989.

Friedel-Crafts acylation reactions have several disadvantages in process chemistry, particularly when the process is conducted on a large manufacturing scale. Disadvantages of Friedel-Crafts acylation reactions in process chemistry include the use of halogenated solvents and/or the use of metal halide catalysts, both of which are associated with environmental risks and/or economic burdens.

Various methods for preparing 3-unsubstituted 2-butyl-5-nitrobenzofurans are also known. For instance, international patent application WO 2007/140989 discloses production of a benzofuran via a pericyclic rearrangement of an O-phenyl-oxime intermediate. In this reaction, the benzofuran is prepared from 4-chloronitrobenzene and 2-hexanone oxime by way of a two-step process. Firstly, the 4-chloronitrobenzene and the oxime are reacted under basic (alkaline) conditions to provide an O-phenyl-oxime intermediate. The intermediate so formed is then extracted (i.e. separated) before being converted (under acidic conditions) to the corresponding benzofuran.

The journal article European Journal of Organic Chemistry, Vol. 9, pages 1491-1509 by Takeda et al (ISSN:1434-193X) discloses various reactions, including the reaction of a certain phenylhydroxylamine with a certain mono-ketone to produce a O-phenyl oxime intermediate, which intermediate may be separately reacted to form a benzofuran via an intramolecular rearrangement reaction.

However, the above-mentioned Takeda et al journal article discloses that it is crucial that an acylating reagent should be employed to promote the intramolecular rearrangement to produce the benzofuran intermediate.

Furthermore, there is no disclosure in the above-mentioned Takeda et al journal article of the reaction of a phenylhydroxylamine with a diketone, to ultimately form a 3-acyl benzofuran. Further, there is no disclosure of the reaction of a 4-nitrophenylhydroxylamine with a ketone (mono- or diketone) to ultimately form a benzofuran. Further still, there is no disclosure of a reaction between a phenylhydroxylamine with a ketone (mono- or diketone) in which a benzofuran is formed without the need to isolate the O-phenyl oxime intermediate formed.

There is a need for alternative benzofuran-forming reactions that provide for more efficient production of benzofurans and/or allow for the preparation of 3-aroylbenzofurans without the need for a Friedel-Crafts acylation step.

The listing or discussion of an apparently prior-published document in this specification should not necessarily be taken as an acknowledgement that the document is part of the state of the art or common general knowledge.

In a first aspect of the invention, there is provided a process for the preparation of a compound of formula I,

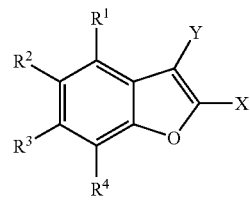

I wherein $R^1$, $R^2$, $R^3$ and $R^4$ independently represent hydrogen, halo, $-NO_2$, $-CN$, $-C(O)_2R^{x1}$, $-OR^{x2}$, $-SR^{x3}$, $-S(O)R^{x4}$, $-S(O)_2R^{x5}$, $-N(R^{x6})R^{x7}$, $-N(R^{x8})C(O)R^{x9}$, $-N(R^{x10})S(O)_2R^{x11}$ or $R^{x12}$;

X represents hydrogen or $C_{1-6}$ alkyl optionally substituted by one or more halo atoms;

Y represents H or $-C(O)-Z$;

Z represents aryl or heteroaryl optionally substituted by one or more substituents selected from $-OR^a$, halo, $-NO_2$, $-CN$, $-C(O)_2R^{a1}$, $-SR^{a3}$, $-S(O)R^{a4}$, $-S(O)_2R^{a5}$, $-N(R^{a6})R^{a7}$, $-N(R^{a8})C(O)R^{a9}$, $-N(R^{a10})S(O)_2R^{a11}$ and $R^{a12}$;

$R^a$ represents an oxy-protecting group, hydrogen or $C_{1-6}$ alkyl optionally substituted by one or more substituents selected from halo, $-C(O)_2R^{b1}$ and $-N(R^{b2})R^{b3}$;

$R^{x1}$, $R^{x2}$, $R^{x3}$, $R^{x6}$, $R^{x7}$, $R^{x8}$, $R^{x9}$, $R^{x10}$, $R^{a1}$, $R^{a3}$, $R^{a6}$, $R^{a7}$, $R^{a8}$, $R^{a9}$, $R^{a10}$, $R^{b1}$, $R^{b2}$ and $R^{b3}$ independently represent hydrogen or $C_{1-6}$ alkyl optionally substituted by one or more halo atoms;

$R^{x4}$, $R^{x5}$, $R^{x11}$, $R^{x12}$, $R^{a4}$, $R^{a5}$, $R^{a11}$ and $R^{a12}$ independently represent $C_{1-6}$ alkyl optionally substituted by one or more halo atoms;

which process comprises reaction of a compound of formula II,

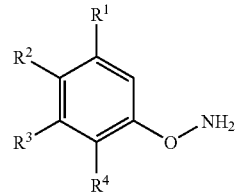

II or a protected derivative or salt thereof, wherein $R^1$, $R^2$, $R^3$, $R^4$ are as defined above, with a compound of formula III,

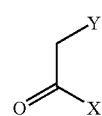

III wherein Y and X are as defined above, which process is hereinafter referred to as "the process of the invention".

In a first embodiment of the invention, there is provided a process for the preparation of a compound of formula I as hereinbefore defined, but characterised in that Y represents —C(O)Z, which process comprises reaction of a compound of formula II as hereinbefore defined, or a protected derivative or salt thereof, with a compound of formula III as hereinbefore defined, but in which Y represents —C(O)Z.

In a further embodiment of the invention, there is provided a process for the preparation of a compound of formula I as hereinbefore defined, which process comprises reaction of a compound of formula II as hereinbefore defined, or a protected derivative or salt thereof, with a compound of formula III as hereinbefore defined, characterised in that the reaction is performed as a "one-pot" procedure.

In another embodiment of the invention, there is provided a process for the preparation of a compound of formula I as hereinbefore defined, but characterised in that $R^2$ represents —$NO_2$, which process comprises reaction of a compound of formula II as hereinbefore defined, or a protected derivative or salt thereof, but in which $R^2$ represents —$NO_2$, with a compound of formula III as hereinbefore defined.

In another embodiment of the invention, there is provided a process for the preparation of a compound of formula I as hereinbefore defined, characterised in that the process is performed in the absence of an acylating reagent. For example, when the process of the invention proceeds via an intermediate of formula XXIV (as defined hereinafter), then that intermediate is not first reacted in the presence of an acylating reagent (such as trifluoroacetic anhydride or trifluoroacetyl triflate) to form an N-acylated intermediate in order to promote the pericyclic cyclisation to form the compound of formula I.

The above-mentioned embodiments of the invention are also referred to herein as the "process of the invention".

The process of the invention may be performed employing salts, solvates or protected derivatives of the compounds of formulae II and III. Compounds of formula I that may thereby be produced may or may not be produced in the form of a (e.g. corresponding) salt or solvate, or a protected derivative thereof.

For instance, it is specifically stated above that a protected derivative or salt of a compound of formula II may be employed in the process. In this respect, specific salts that may be mentioned include acid salts, such as hydrogen halide salts (e.g. HCl) and specific protecting groups that may be mentioned include suitable protecting groups for the hydroxylamine moiety, such as imino-protecting groups or amino-protecting groups, for example as defined by compounds of formula IIA and IIB,

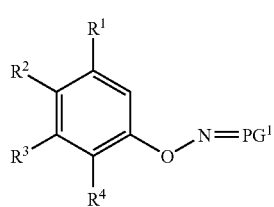

IIA

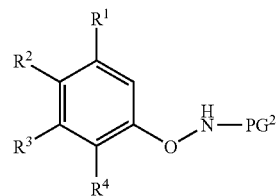

IIB respectively, wherein:

$PG^1$ represents an imino-protecting group (i.e. a protecting group for the amino moiety that results in an imino functional group), such as =$C(R^{q1})OR^{q2}$ (so forming a protected hydroxylamine group that is —O—N=$C(R^{q1})OR^{q2}$), in which $R^{q1}$ and $R^{q2}$ independently represent $C_{1-6}$ alkyl, and more preferably represent $C_{1-3}$ alkyl. Most preferably $R^{q1}$ represents methyl and/or $R^{q2}$ represents ethyl (so forming, for example, a compound of formula IIA in which the protected hydroxylamine group is —O—N=$C(CH_3)OCH_2CH_3$). As stated hereinafter, compounds of formula IIA may be exist as geometric isomers, i.e. cis and trans isomers about the imino double bond;

$PG^2$ represents an amino protecting group (i.e. a protecting group that results in the amino moiety being a secondary amino group) such as a protecting group that provides an amide (e.g. N-acetyl), N-alkyl (e.g. N-allyl or optionally substituted N-benzyl), N-sulfonyl (e.g. optionally substituted N-benzenesulfonyl) or, more preferably a carbamate or urea.

Hence, $PG^2$ may represent:

—$C(O)R^{r1}$ (in which $R^{r1}$ preferably represents $C_{1-6}$ alkyl or optionally substituted aryl);

$C_{1-6}$ alkyl, which alkyl group is optionally substituted by one or more substituents selected from optionally substituted aryl;

—$S(O)_2R^{r2}$ (in which $R^{r2}$ preferably represents optionally substituted aryl); or, preferably, —$C(O)OR^{r3}$ (in which $R^{r3}$ preferably represents optionally substituted aryl or, more preferably, $C_{1-6}$ (e.g. $C_{1-4}$) alkyl, e.g. tert-butyl (so forming, for example, a tert-butoxycarbonyl protecting group, i.e. when taken together with the amino moiety, a tert-butylcarbamate group);

—$C(O)N(R^{r4})R^{r5}$ (in which, preferably, $R^{r4}$ and $R^{r5}$ independently represent hydrogen, $C_{1-6}$ alkyl, optionally substituted aryl or —$C(O)R^{r6}$, and $R^{r6}$ represents $C_{1-6}$ alkyl or optionally substituted aryl).

When used herein (e.g. in the context of protecting groups such as those defined by $PG^2$), the term "optionally substituted aryl" preferably refers to "optionally substituted phenyl", in which the optional substituents are preferably selected from halo, —$NO_2$, —OH and/or —$OC_{1-6}$ alkyl.

When protected derivates of compounds of formula II are employed in the process of the invention, then it is preferred that compounds of formula IIA are employed.

Advantageously, when protected derivatives of compounds of formula II (e.g. compounds of formula IIA or IIB) or salts of compounds of formula II (e.g. acid salts such as a hydrogen halide salt, e.g. HCl) are employed in the process of the invention, then the step of deprotection to the unprotected compound of formula II, or the step of neutralisation (e.g. by basification of the acid salt) to the free base of the compound of formula II, need not be performed separately, e.g. prior to the process of the invention. Such steps may advantageously be performed in the same "pot" as the process of the invention, i.e. the deprotection or neutralisation may occur whilst the reaction of the process of the invention also occurs, thereby providing compounds of formula I that are not in a protected form and/or not in the form of a salt.

Unless otherwise specified, alkyl groups as defined herein may be straight-chain or, when there is a sufficient number (i.e. a minimum of three) of carbon atoms be branched-chain, and/or cyclic. Further, when there is a sufficient number (i.e. a minimum of four) of carbon atoms, such alkyl groups may also be part cyclic/acyclic. Such alkyl groups may also be saturated or, when there is a sufficient number (i.e. a minimum of two) of carbon atoms, be unsaturated.

The term "aryl", when used herein, includes $C_{6-10}$ groups. Such groups may be monocyclic, bicyclic or tricyclic and, when polycyclic, be either wholly or partly aromatic. $C_{6-10}$ aryl groups that may be mentioned include phenyl, naphthyl, and the like. For the avoidance of doubt, the point of attachment of substituents on aryl groups may be via any carbon atom of the ring system.

The term "heteroaryl", when used herein, includes 5- to 14-membered heteroaryl groups containing one or more heteroatoms selected from oxygen, nitrogen and/or sulfur. Such heteroaryl group may comprise one, two or three rings, of which at least one is aromatic. Substituents on heteroaryl groups may, where appropriate, be located on any atom in the ring system including a heteroatom. The point of attachment of heteroaryl groups may be via any atom in the ring system including (where appropriate) a heteroatom. Examples of heteroaryl groups that may be mentioned include pyridyl, pyrrolyl, quinolinyl, furanyl, thienyl, oxadiazolyl, thiadiazolyl, thiazolyl, oxazolyl, pyrazolyl, triazolyl, tetrazolyl, isoxazolyl, isothiazolyl, imidazolyl, pyrimidinyl, indolyl, pyrazinyl, indazolyl, pyrimidinyl, quinolinyl, benzoimidazolyl and benzthiazolyl.

The term "halo", when used herein, includes fluoro, chloro, bromo and iodo.

It is stated herein that $R^a$ may represent an oxy-protecting group. Oxy-protecting groups that may be mentioned include trialkylsilyl and diarylalkyl-silyl groups (e.g. tert-butyldimethylsilyl, tert-butyldiphenylsilyl or trimethylsilyl), tetrahydropyranyl, —C(O)$R^{r1}$, $C_{1-6}$ alkyl (which alkyl group is optionally substituted by one or more substituents selected from optionally substituted aryl, so forming an alkylaryl group), —S(O)$_2$$R^{r2}$, —C(O)O$R^{r3}$ and —C(O)N($R^{r4}$)$R^{r5}$, in which $R^{r1}$, $R^{r2}$, $R^{r3}$, $R^{r4}$ and $R^{r5}$, as well as preferred optional substituents on any relevant aryl groups, are as hereinbefore defined. The skilled person will appreciate that in compounds of formula I, when $R^a$ represents $C_{1-6}$ alkyl, certain of these groups may be considered to be protecting groups (e.g. allylic groups). Other oxy-protecting groups include salts, for example an inorganic metal salt, such as a group II or, preferably a group I metal salt (e.g. a sodium or potassium salt, so forming for example a —O$^-$Na$^+$ or —O$^-$K$^+$ moiety).

Most preferred oxy-protecting groups include —C(O)$R^{r1}$ groups, preferably in which $R^{r1}$ represents a $C_{1-6}$ alkyl group, so forming an alkylcarbonyl groups (e.g. methyl- and ethylcarbonyl groups), and alkylaryl groups (e.g. benzyl optionally substituted as hereinbefore defined). It is most preferred that, when $R^a$ represents an oxy-protecting group, then it represents an alkylaryl group, especially a benzyl group, which is optionally substituted as defined herein, but preferably unsubstituted.

Compounds employed in or produced by the processes described herein (i.e. those involving the process of the invention) may exhibit tautomerism. The process of the invention therefore encompasses the use or production of such compounds in any of their tautomeric forms, or in mixtures of any such forms.

Similarly, the compounds employed in or produced by the processes described herein (i.e. those involving the process of the invention) may also contain one or more asymmetric carbon atoms and may therefore exist as enantiomers or diastereoisomers, and may exhibit optical activity. The process of the invention thus encompasses the use or production of such compounds in any of their optical or diastereoisomeric forms, or in mixtures of any such forms.

Further, the compounds employed in or produced by the processes described herein (e.g. compounds of formula IIA as hereinbefore defined) may contain double bonds and may thus exist as E (entgegen) and Z (zusammen) geometric isomers about each individual double bond. All such isomers and mixtures thereof are included within the scope of the invention.

According to a further aspect of the invention, there is provided processes for the preparation of compounds of formula II and III (or derivatives thereof), as well as processes for the preparation of intermediate compounds to compounds of formula II and III.

Compounds of formula II, or salts thereof, may be prepared by deprotection of a corresponding compound of formula IIA or IIB, under standard conditions known to those skilled in the art. For instance, for deprotection of compounds of formula IIA, standard hydrolysis conditions may be employed, e.g. the presence of an acid (e.g. a hydrogen halide, such as HBr or, preferably, HCl) in an aqueous solution (the acid may also be an inorganic acid such as phosphorus or sulphuric acid). Such conditions may result in a salt of a (non-protected derivative of a) compound of formula II (e.g. a relevant hydrogen halide salt), or, the free base version of such a compound of formula II (for instance, when the salt form is neutralised, e.g. by basification).

Compounds of formula IIB or, preferably, IIA may be prepared by reaction of a compound of formula IV,

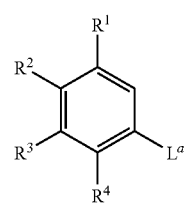

IV wherein $L^a$ represents a suitable leaving group, such as a sulfonate group (e.g. —OS(O)$_2$CF$_3$, —OS(O)$_2$CH$_3$ or —OS(O)$_2$PhMe) or, more preferably halo (e.g. bromo, fluoro or, preferably, chloro), and $R^1$, $R^2$, $R^3$ and $R^4$ are as hereinbefore defined, with a compound of formula V (in the case of preparation of compounds of formula IIA),

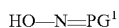

HO—N=PG$^1$     V wherein PG$^1$ is as hereinbefore defined, or a compound of formula VI (in the case of preparation of compounds of formula IIB),

HO—N(H)—PG$^2$     VI wherein PG$^2$ is as hereinbefore defined, for example under standard aromatic substitution reaction conditions. For instance, the aromatic substitution reaction may be performed in the presence of a polar aprotic solvent (such as dimethylformamide). In this context, other polar aprotic solvents that may be mentioned include tetrahydrofuran, dimethylsulfoxide, diethyl ether and dioxane. However, it has now been found that this process step may also be performed in a mixture of solvents, only one of which is a polar aprotic solvent (and the other is a non-polar solvent). Hence, in another aspect of the invention, there is provided such a process in the presence of a non-polar solvent, such as a non-polar aprotic solvent, which solvent is employed in addition to the polar aprotic solvent as defined above (and which is preferably dimethylformamide). Preferred non-polar aprotic solvents include toluene, but may be any solvent that may be employed to extract compounds of formula V or VI (e.g. from a reaction mixture as defined hereinafter).

Advantageously, in this aspect of the invention (i.e. the process for the preparation of compounds of formula IIA or IIB), a solution containing the compound of formula V or VI (whichever is employed), for example a solution obtained by the extraction from a reaction mixture (following the preparation of those compounds of formula V or VI), need not be concentrated by the partial or complete evaporation of the solvent (i.e. advantageously, solvent need not be removed). Rather, a polar aprotic solvent (e.g. DMF) may preferably be added directly to a solution of the compound of formula V or VI without complete removal (and most preferably, without any removal) of any non-polar solvent, for example that which is employed in an extraction.

Certain compounds (and/or processes to obtain compounds) of formula III are novel per se. Hence, in a further aspect of the invention there is provided a compound of formula III as hereinbefore defined, but in which Y represents —C(O)—Z. Preferably such a compound of formula III is also one in which X represents butyl (e.g. n-butyl). Such intermediates, which may be novel, may advantageously be employed in the process of the invention.

Compounds of formula III in which Y represents —C(O)—Z may be prepared by:

(i) reaction of a compound of formula VII,

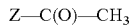     VII wherein Z is as hereinbefore defined, with a compound of formula VIII,

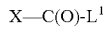     VIII wherein $L^1$ represents a suitable leaving group, such as halo (e.g. bromo, chloro or iodo) or, more preferably, —$OC_{1-6}$ alkyl (e.g. —$OCH_3$ or, preferably, —$OCH_2CH_3$), and X is as hereinbefore defined, preferably in the presence of a suitable base, such as an alkali metal hydride (e.g. KH, $CaH_2$ or, preferably, NaH), an organolithium base (e.g. n-, s- or t-butyllithium or, preferably, lithium diisopropylamide), another alkali metal based base (e.g. $Na_2CO_3$, $K_2CO_3$, $K_3PO_4$, t-BuONa, t-BuOK or, preferably, $CH_3ONa$), or mixtures of bases, and (a) suitable solvent(s) (such as tetrahydrofuran (THF), toluene and/or dimethylformamide; a polar aprotic solvent such as THF is particularly preferred) under standard conditions, such as at room temperature or elevated temperature, such as about 65° C.;

(ii) reaction of a compound of formula IX,

     IX wherein X is as hereinbefore defined, with a compound of formula X,

     X wherein Z and $L^1$ are as hereinbefore defined, for example under reaction conditions such as those hereinbefore described in respect of preparation of compounds of formula III (process step (i) above);

(iii) for compounds of formula III, in which Y represents —C(O)—Z and Z represents aryl or heteroaryl substituted by —OH, reaction of a corresponding compound of formula XI,

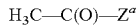     XI wherein $Z^a$ represents aryl or heteroaryl substituted with —O—C(O)—X (in which X is as hereinbefore defined), with base, for instance a base and reaction conditions such as those hereinbefore defined in respect of preparation of compounds of formula III (process step (i) above). For the avoidance of doubt, the —O—C(O)—X substituent of the compound of formula XI is converted to the —OH substituent of the compound of formula III;

(iv) decarboxylation of a compound of formula XII,

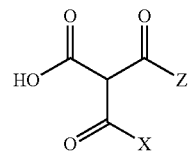     XII or a protected (e.g. a —C(O)OH protected) derivative thereof (such as an ester of a —C(O)OH), wherein X and Z are as hereinbefore defined, under standard decarboxylation reaction conditions known to those skilled in the art;

(v) hydrolysis of a compound of formula XIII,

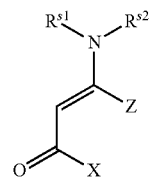     XIII wherein $R^{s1}$ and $R^{s2}$ independently represent hydrogen, $C_{1-6}$ alkyl optionally substituted by one or more halo atoms, or $R^{s1}$ and $R^{s2}$ are linked together to form, together with the nitrogen atom to which they are necessarily attached, a 4- to 8-membered (e.g. 5- or 6-membered) heterocycloalkyl group (optionally containing a further heteroatom, such as a further nitrogen or oxygen heteroatom, and which heterocycloalkyl group is optionally substituted by one or more substituents selected from halo or $C_{1-6}$ alkyl), such as a piperidinyl or pyrrolidinyl ring, and X and Z are as hereinbefore defined, under standard conditions, for example in the presence of an aqueous acid (e.g. an aqueous solution of a hydrogen halide);

(vi) for compounds of formula III in which Z preferably represents aryl (e.g. phenyl) substituted (preferably in the ortho- or, more preferably in the para position) with —$SR^{a3}$, —$N(R^{a6})R^{a7}$ or preferably, —$OR^a$, reaction of a compound of formula XIV,

     XIV wherein Z is as hereinbefore defined, and preferably represents aryl (e.g. phenyl) substituted (preferably in the ortho- or, more preferably in the para position) with —$SR^{a3}$, —$N(R^{a6})R^{a7}$ or, preferably, —$OR^a$ and $R^a$, $R^{a3}$, $R^{a6}$ and $R^{a7}$ are as hereinbefore defined, with either:

(A) a compound of formula XV,

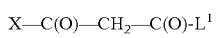     XV or a protected derivative (e.g. acetal) thereof, wherein X is as hereinbefore defined, and $L^1$ is as hereinbefore defined and preferably represents halo (e.g. bromo or, preferably, chloro); or (B) a compound of formula XVI,

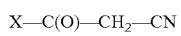
$$X\text{---}C(O)\text{---}CH_2\text{---}CN \qquad \text{XVI}$$

or a protected derivative (e.g. acetal) thereof, wherein X is as hereinbefore defined, under standard reaction conditions known to those skilled in the art, for instance under Friedel-Crafts acylation reaction conditions, e.g. in the presence of a suitable acid such as a protic acid (e.g. sulfuric acid) or, preferably, a Lewis acid such as $AlCl_3$. The skilled person will appreciate that when a protected derivative (e.g. an acetal protected derivative) of a compound of formula XV or XVI is employed, the resultant compound of formula III may need to be deprotected under standard conditions. Protecting groups that may be employed include acetals, which may protect any carbonyl group present. Acetal derivatives of compounds of formula XV or XVI that may be mentioned include compounds of formula $X\text{---}C(OR^{v1})_2\text{---}CH_2\text{---}C(O)\text{-}L^1$ and $X\text{---}C(OR^{v1})_2\text{---}CH_2\text{---}CN$, in which each $R^{v1}$ independently represents $C_{1-6}$ alkyl, or, the two $R^{v1}$ groups may be linked together to form, together with the oxygen atoms to which they are necessarily attached, a 4- to 7-membered (e.g. 5- or 6-membered) ring (i.e. a cyclic acetal). Such acetal protecting groups may be introduced by the reaction of a compound of formula XV or XVI in the presence of an appropriate alcohol (e.g. of formula $HO\text{---}R^{v1}$) or a diol (e.g. of formula $HO\text{---}R^{v1}\text{---}R^{v1}\text{---}OH$, in which the relevant $R^{v1}$ groups are linked together) in the case of the formation of cyclic acetals, under appropriate acid or base catalysis conditions. Such acetal protecting groups may be removed under standard conditions, for example by hydrolysis e.g. in the presence of acid;

(vii) reduction of a compound of formula XVIA,

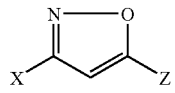

or a compound of formula XVIB,

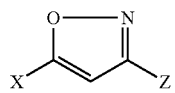

wherein (in both cases) X and Z are as hereinbefore defined, in the presence of aqueous acid, under standard conditions, for example reduction by hydrogenolysis, which may be performed in the presence of a suitable catalyst system. The catalyst may be a precious transition metal, for example platinum, ruthenium, nickel (e.g. Raney nickel) or, especially, palladium. The metal may be used as such in powder form, as its oxide or hydroxide or, preferably, on a suitable support, such as powdered charcoal. Typically, palladium on charcoal is used (e.g. 5% Pd/C). Advantageously, when there is another group present that requires reduction to form the compound of formula III, then essentially two steps may be performed in "one-pot". For instance, when Z represents aryl or heteroaryl substituted by $\text{---}OR^a$ in which $R^a$ represents a protecting group susceptible to cleavage via a hydrogenolysis reaction, e.g. a benzyl protecting group, then such a group may also be cleaved by such a hydrogenolysis reaction to form a corresponding $\text{---}OH$ group, at the same time as the isoxazole moiety undergoes hydrogenolysis to the appropriate diketone (of formula III).

Compounds of formula V in which $PG^1$ represents $=C(R^{q1})OR^{q2}$, may be prepared by reaction of hydroxylamine, or a salt thereof (e.g. a hydrogen halide salt, such as HCl) with a compound of formula XVII,

$$HN=C(R^{q1})OR^{q2} \qquad \text{XVII}$$

wherein $R^{q1}$ and $R^{q2}$ are as hereinbefore defined, under standard reaction conditions. The reaction mixture to obtain such a product may be extracted with a suitable solvent, such as a non-polar solvent (e.g. toluene).

Compounds of formula XI may be prepared by reaction of a compound of formula XVIII,

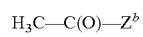
$$H_3C\text{---}C(O)\text{---}Z^b \qquad \text{XVIII}$$

wherein $Z^b$ represents aryl or heteroaryl substituted with $\text{---}OH$, with a compound of formula VIII as defined above, under standard conditions, for example, such as those described hereinbefore in respect of preparation of compounds of formula III (process step (i) above).

Compounds of formula XII may be prepared by reaction of a compound of formula X as defined above, with a compound of formula XIX,

$$X\text{---}C(O)\text{---}CH_2\text{---}C(O)OH \qquad \text{XIX}$$

or a protected (e.g. a $\text{---}C(O)OH$ protected) derivative thereof (such as an ester of a $\text{---}C(O)OH$), wherein X is as hereinbefore defined, under standard reaction conditions, for example such as those hereinbefore described in respect of preparation of compounds of formula III (process step (i) above).

Compounds of formula XIII may be prepared by reaction of a compound of formula XX,

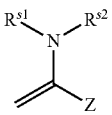

wherein Z, $R^{s1}$ and $R^{s2}$ are as hereinbefore defined, with a compound of formula VIII as hereinbefore defined, under reaction conditions such as those hereinbefore described in respect of preparation of compounds of formula III (process step (i)), and preferably in which, when a base is employed, it is a weak base, such as $Na_2CO_3$, $K_2CO_3$, $K_3PO_4$, t-BuONa, t-BuOK, preferably, $CH_3ONa$, or mixtures thereof.

Compounds of formula XVIA and XVIB may be prepared by reaction of corresponding compounds of formula III in which Y represents $\text{---}C(O)\text{---}Z$ with hydroxylamine (or a salt thereof, e.g. HCl), under standard condensation reaction conditions. Such a process step starts with compounds of formula III, and hence when such a process step is taken in conjunction with process step (vii) above (in respect of preparation of compounds of formula III), then the resultant products are also compounds of formula III. Such a sequence of steps, however, are useful e.g. in obtaining compounds of formula III in a purer form. Essentially, therefore, these two steps taken in conjunction may provide a process for the purification (by which we mean the removal of any impurity, such as most of the impurities, including residual reactants) of compounds of formula III.

Compounds of formula XVII may be prepared by reaction of a compound of formula XXI,

   XXI wherein $R^{q1}$ is as hereinbefore defined, with a compound of formula XXII,

   XXII wherein $R^{q2}$ is as hereinbefore defined, under standard reaction conditions, for example, in the presence of an acid, such as a hydrogen halide (e.g. HCl).

Compounds of formula XX may be prepared by reaction of a compound of formula VII as defined above, with a compound of formula XXIII,

   XXIII wherein $R^{s1}$ and $R^{s2}$ are as hereinbefore defined, under dehydration standard reaction conditions, e.g. in the presence of an appropriate acid catalyst (e.g. a non-aqueous acid, such as para-toluene sulfonic acid, or the like).

Compounds of formulae IV, VI, VII, VIII, IX, X, XIV, XV, XVI, XVIII, XIX, XXI, XXII and XXIII (and certain other compounds, for instance, certain compounds of formulae II, III and V), and derivatives thereof (e.g. protected derivatives), may be commercially available, are known in the literature or may be obtained by conventional synthetic procedures, in accordance with known techniques, from readily available starting materials using appropriate reagents and reaction conditions.

Any of the processes described herein may advantageously be employed in conjunction (i.e. in sequence). For example, processes for the preparation of compounds of formula IIA may consist of, first, a process for the preparation of a compound of formula V as described herein (i.e. comprising reaction of a compound of formula XVII with hydroxylamine, or a salt thereof), followed by a process for the preparation of the compound of formula IIA (i.e. comprising reaction of a compound of formula IV with a compound of formula V so prepared). Further, processes for the preparation of compounds of formula II and/or III (or derivatives thereof) may advantageously be employed in conjunction with the process of the invention.

Substituents on compounds of formula I, II, III, or any relevant intermediate compounds to such compounds (or salts, solvates or derivatives thereof), for instance substituents defined by $R^1$, $R^2$, $R^3$, $R^4$, or substituents on Z, may be modified one or more times, before, after or during the processes described above by way of methods that are well known to those skilled in the art. Examples of such methods include substitutions, reductions, oxidations, alkylations, acylations, hydrolyses, esterifications, etherifications, halogenations, nitrations, diazotizations or combinations of such methods. In this manner certain compounds of formula I, II or III (or derivative thereof) may be converted to other compounds of formula I, II or III (or derivative), respectively. For instance, a compound of formula IV in which $R^2$ represents —$NO_2$ may be employed (which compound may be better suited to a nucleophilic aromatic substitution reaction of a compound of formula IV with a compound of formula V) to synthesis a compound of formula IIA in which $R^2$ is also —$NO_2$. However, such a —$NO_2$ group may be reduced to an amino group before or after the process of the invention to form a corresponding compound of formula I in which $R^2$ represents amino. Such an amino group may not have been suited to the above-mentioned nucleophilic aromatic substitution reaction, if initially an amino substituted compound of formula IV was deployed. Likewise a compound of formula III in which Z represents aryl or heteroaryl substituted by —$NH_2$ may be employed in the process of the reaction, but that amino group may be converted to a diazonium salt, and then subsequently to, for example, a —OH group, before or after the process of the reaction.

It is stated herein that specific functional groups may be protected. It will also be appreciated by those skilled in the art that, in the processes described above, other functional groups of intermediate compounds may be, or may need to be, protected by protecting groups.

In any event, functional groups which it is desirable to protect include hydroxy (e.g. $R^a$ may represent an oxy-protecting group). Suitable protecting groups for hydroxy include trialkylsilyl and diarylalkyl-silyl groups (e.g. tert-butyldimethylsilyl, tert-butyldiphenylsilyl or trimethylsilyl), tetrahydropyranyl and alkylcarbonyl groups (e.g. methyl- and ethylcarbonyl groups). However, most preferred protecting groups for hydroxy include alkylaryl groups, such as optionally substituted benzyl.

The protection and deprotection of functional groups may take place before or after any of the reaction steps described hereinbefore.

Protecting groups may be removed in accordance with techniques which are well known to those skilled in the art and as described hereinafter.

The use of protecting groups is described in "Protective Groups in Organic Chemistry", edited by J. W. F. McOmie, Plenum Press (1973), and "Protective Groups in Organic Synthesis", 3rd edition, T. W. Greene & P. G. M. Wutz, Wiley-Interscience (1999).

The skilled person will appreciate that the process of the invention may proceed via an O-phenyl oxime intermediate, i.e. a compound of formula XXIV,

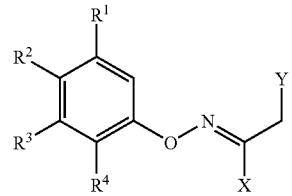

XXIV wherein $R^1$ to $R^4$, X and Y are as hereinbefore defined, which intermediate then undergoes a pericyclic rearrangement, ultimately forming a benzofuran ring. It is hereinbefore stated that in an embodiment of the invention, the process of the invention is performed in the absence of an acylating agent. In this instance, when the process of the invention proceeds via an intermediate of formula XXIV, then the phenyl oxime intermediate of formula XXIV does not first react with an acylating reagent to form an N-acyl group at the imino nitrogen (the relevant imino functional group being converted to enamino functional group), for example as depicted by the following compound of formula XXIVA,

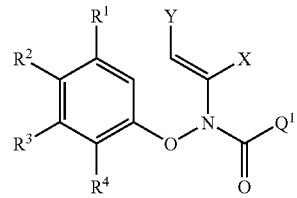

XXIVA or another enamino equivalent thereof (for example, when X represents an alkyl group, the double bond of the enamino moiety may be adjacent the X group), wherein $Q^1$ represents, for example, a $C_{1-6}$ alkyl group optionally substituted by one or more fluoro atoms (so forming, for example a —$CF_3$ group) and $R^1$ to $R^4$, X and Y are as hereinbefore defined.

Rather, the pericyclic rearrangement of the compound of formula XXIV takes place in the absence of an acylating reagent and hence does not proceed via an intermediate of formula XXIVA. Rather, the pericyclic rearrangement is performed under reaction conditions such as those described herein, for example in the presence of acid, such as a weak organic acid as described herein.

Such an intermediate may be separated (e.g. isolated) in the process of the invention and/or reaction conditions may subsequently be modified. That is, in a first reaction step, a compound of formula II, as hereinbefore defined, may be reacted with a compound of formula III, as hereinbefore defined, to form an intermediate compound of formula XXIV and, in a subsequent reaction step, the intermediate of formula XXIV may undergo reaction (i.e. a pericyclic rearrangement reaction) to form the compound of formula I. Hence, such an embodiment essentially consists of two (e.g. distinct/ separate) reaction steps. In such an embodiment, the intermediate compound of formula XXIV may be separated (e.g. extracted, optionally isolated from any impurities, and any solvent optionally removed) from the reaction mixture and/or the subsequent reaction step may be performed under modified reaction conditions (e.g. in the presence of a different, or 'fresh', solvent and/or in the presence of additional reagents).

However, advantageously, any intermediate formed in the process of the present invention (such as an intermediate of formula XXIV) need not be separated and/or reaction conditions need not be modified in order to promote the benzofuran-forming reaction. In essence, therefore, the reaction may be performed as a "one-pot" procedure. Such a "one-pot" procedure is particularly preferred in the case where compounds of formula I in which Y represents H (and/or compounds of formula I in which $R^2$ represents —$NO_2$) are required and/or desired.

Thus, in particular embodiments of the invention, the reaction is performed without separation (e.g. isolation) of any intermediates. In alternative embodiments of the invention, the reaction is conducted without modification of the reaction conditions.

Where it is stated that the reaction is performed without separation of intermediates, we mean that any intermediate that may be formed by reaction of the starting reagents, is not isolated, e.g. in a purified state (whether or not the intermediate is still in the presence of solvent and/or residual starting materials or other impurities). In this context, we therefore include that the any intermediate is not extracted from the reaction of the starting materials. Where it is stated that the reaction conditions need not be modified, we encompass reactions in which the solvent need not be changed and/or that further reagents need not be added.

Certain compounds of formula XXIV are novel per se. Hence, in a further aspect of the invention, there is provided a compound of formula XXIV as hereinbefore defined, but in which Y represents —C(O)—Z. Such compounds may be isolated or may be formed in situ (as an intermediate, which reacts to form another product, e.g. a compound of formula I via an intramolecular cyclisation reaction) and may not therefore be isolated. In yet another aspect of the invention, there is provided a process for the preparation of a compound of formula I as hereinbefore defined, but in which Y represents —C(O)—Z, which comprises reaction, for example an intramolecular reaction (i.e. pericyclic rearrangement), of a compound of formula XXIV in which Y represents —C(O)—Z. Such a reaction may be performed in the absence of an acylating reagent, and may for example be performed under the reaction conditions described herein.

The process of the invention (i.e. the benzofuran-forming reaction of a compound of formula II with a compound of formula III) is preferably performed in the presence of an acid, such as a weak organic acid (e.g. formic acid or, preferably, acetic acid) and/or an inorganic acid, such as any suitable mineral acid, or suitable salts thereof (for example, nitric acid, sulfuric acid, or salts thereof, such as sodium hydrogen sulphate, or, more preferably, a hydrogen halide acid, e.g. HBr). Mixtures of acids may also be employed, for instance, a mixture of a weak organic acid and an inorganic acid (e.g. HBr and acetic acid). Further, when an acid is employed, then that acid may be a component of an aqueous solution. By "weak organic acid", we mean that the organic acid has a pKa (at about 25° C.) of from about 2 to about 6 (e.g. from about 3 to about 5).

The process of the invention may be performed in the presence of a suitable solvent, for example water or an organic solvent such as toluene, tetrahydrofuran, diethyl ether, dioxane, dimethylformamide, dimethylsulfoxide, or, preferably an alcohol (such as methanol or ethanol), or mixtures thereof (including biphasic solvent systems, such as a mixture of water and an organic solvent). However, when a weak organic acid is employed (whether it is as the only acid component or as a component of a mixture of acids) in the reaction mixture, then that acid may serve as both the reagent and solvent. In such an instance, advantageously, the separate use of a solvent in the reaction mixture is circumvented (although, as stated above, a mixture of such a organic acid and another suitable solvent, as defined above, may be employed). In particular, weak organic acids that have a relatively low boiling point may serve as the reagent and solvent, for instance those organic acids with a boiling point of less than 150° C. (e.g. formic or, more preferably, acetic acid). When, for instance, a weak organic acid (e.g. that serves as reagent and solvent) is employed, then it may be employed as a solution (e.g. in water or an organic solvent) or, e.g. more preferably, it is employed "neat". For instance, when acetic acid is employed, then it may be glacial acetic acid.

When a solvent, or a weak organic acid that serves as a solvent, is employed, then it may be present in any suitable volume. However, it is preferred that the concentration of the compound of formula II in the solvent/weak organic acid solvent is from about 0.1 M to about 5 M, preferably from about 0.5 M to about 2 M (e.g. between about 0.6 M and 1.5 M).

In the event that the compounds of formula II and III are added to the reaction mixture at the same time, then the concentration of the reagents in the solvents will be higher (in accordance with the molar ratios of the compounds of formulae II and III in the reaction mixture; see below). However, it is preferred that the compound of formula III is added to the compound of formula II (which latter is preferably already in the presence of a solvent or weak organic acid that serves as a solvent), especially when Y represents H in the compound of formula III. However, particularly when Y represents —C(O)—Z in the compound of formula III, then it is particularly preferred that a compound of formula II is added to a compound of formula III (the latter preferably already in the presence of a solvent or weak organic acid that serves as a solvent). Such an order of addition may aid the regioselectivity of the initial intermolecular reaction (for instance, when a compound of formula III in which Y represents —C(O)Z is employed) and/or, in the case where the reaction proceeds via an intermediate compound of formula XXIV, this order of addition may also aid the efficiency of the subsequent intramolecular reaction forming the benzofuran ring.

The process of the reaction may be performed at any suitable reaction temperature, for instance at room or elevated temperature. In certain preferred embodiments of the invention, (e.g. when the reaction takes place in the presence of a mixture of a weak organic acid and strong inorganic acid) the reaction may be performed at room temperature (e.g. for a period of time, such as about 6 hours), or, (e.g. when the reaction takes place in the presence of a weak organic acid solvent) the reaction may be performed at elevated temperature (e.g. at above 50° C., such as between about 60° C. to about 80° C.) for a period of time (such as about 3 hours, or, any suitable period of time up to about 25 hours) followed by, if necessary, an increase in reaction temperature (e.g. to at least 80° C., for instance from about 90° C. to about 118° C. (e.g. such as about 110° C., e.g. about 100° C.)), for a period of time (such as any suitable period of time up to about 25 hours, for instance, 22 hours).

The skilled person will appreciate that the temperature may only be increased up to the boiling point of the solvent system (which may comprise a weak organic acid solvent), for instance, when acetic acid is employed, the reaction temperature may only be increased up to about 118° C. Hence, the preferred temperature conditions of the process of the invention are particularly applicable when the process of the reaction is performed in the presence of acetic acid. However, when the process of the reaction is performed in the presence of other weak organic acids (or otherwise another suitable solvent), such as formic acid, the skilled person will appreciate that the preferred reaction temperature conditions referred to herein may be varied, for example in accordance with differing boiling points.

The process of the invention may also be conducted under conditions that provide an alternative to typical reaction conditions where elevated temperatures are necessary and/or desired. For instance, microwave irradiation conditions may be employed. By 'microwave irradiation conditions', we include reactions in which such conditions promote a thermally induced reaction (for instance at elevated temperature as hereinbefore described) and/or in which such conditions promote a non-thermally induced reaction (i.e. the reaction is essentially induced by the microwaves). Hence, such reaction conditions are not necessarily accompanied by an increase in temperature. The skilled person will appreciate (and be able to non-inventively determine) that the length of reaction time may be altered (e.g. reduced) when employing such reaction conditions.

The process of the invention may also be conducted under pressure, for instance, under a pressure greater than that of normal atmospheric pressure, for example, at a pressure of up to about 5 or 6 bars. Again, the skilled person will appreciate (and be able to non-inventively determine) that the length of reaction time may be altered (e.g. appropriately reduced) when employing such reaction conditions.

The process of the invention may be performed in the presence of any quantity of each of the compounds of formulae II and III. However, it is preferably performed in the presence of compounds of formulae II and III that are in a molar ratio of from about 3:2 to about 2:3, and most preferably in a molar ratio of from about 1.1:1 to about 1:1.1 (e.g. about 1:1).

Preferred compounds of formula I that may be prepared by the process of the invention include those in which:
$R^1$, $R^2$, $R^3$ and $R^4$ independently represent hydrogen, halo, —$NO_2$, —CN, —C(O)$_2R^{x1}$, —N($R^{x6}$)$R^{x7}$ or —N($R^{x10}$)S(O)$_2 R^{x11}$;

X represents $C_{1-6}$ alkyl;
Z represents heteroaryl or, preferably aryl (e.g. phenyl) optionally substituted by one or more substituents selected from —OR$^a$, —$NO_2$, —CN, —C(O)$_2R^{a1}$ and —N($R^{a6}$)$R^{a7}$;
$R^a$ represents an oxy-protecting group, hydrogen or $C_{1-4}$ (e.g. $C_{1-3}$) alkyl optionally substituted by one or more substituents selected from —N($R^{b2}$)$R^{b3}$;
$R^{x1}$, $R^{x2}$, $R^{x3}$, $R^{x6}$, $R^{x7}$, $R^{x8}$, $R^{x9}$, $R^{x10}$, $R^{a1}$, $R^{a3}$, $R^{a6}$, $R^{a7}$, $R^{a8}$, $R^{a9}$, $R^{a10}$, $R^{b1}$, $R^{b2}$ and $R^{b3}$ independently represent hydrogen or $C_{1-4}$ alkyl optionally substituted by one or more halo atoms;
$R^{x4}$, $R^{x5}$, $R^{x11}$, $R^{x12}$, $R^{a4}$, $R^{a5}$, $R^{a11}$ and $R^{a12}$ independently represent $C_{1-4}$ alkyl optionally substituted by one or more halo atoms Further preferred compounds of formula I that may be prepared by the process of the invention include those in which:
any three of $R^1$, $R^2$, $R^3$ and $R^4$ (preferably $R^1$, $R^3$ and $R^4$) represent hydrogen;
one of $R^1$, $R^2$, $R^3$ and $R^4$ (preferably $R^2$) represents a substituent selected from halo, —CN, —C(O)$_2R^{x1}$, preferably, —N($R^{x10}$)S(O)$_2R^{x11}$ or, more preferably, —$NO_2$ or —N($R^{x6}$)$R^{x7}$;
$R^{x1}$ represents H or $C_{1-3}$ alkyl (e.g. propyl, such as isopropyl);
$R^{x6}$, $R^{x7}$ and $R^{x10}$ independently represent hydrogen;
$R^{x11}$ represents $C_{1-2}$ alkyl (e.g. methyl);
when Z represents phenyl, such a group may be unsubstituted or is preferably substituted, for example by one or two (e.g. one) substitutent(s) in the ortho or, preferably in the para position;
substituents on Z groups (e.g. when Z represents phenyl) are preferably selected from —CN, —C(O)$_2R^{a1}$, preferably, —$NO_2$, —N($R^{a6}$)$R^{a7}$, halo (e.g. iodo) and, more preferably, —OR$^a$;
$R^a$ represents an oxy-protecting group, hydrogen or $C_{1-3}$ alkyl (e.g. ethyl or, preferably, propyl or methyl) optionally substituted by one or more substituents selected from —N($R^{b2}$)$R^{b3}$ (so forming, for example a —(CH$_2$)$_2$—N($R^{b2}$)$R^{b3}$ or, preferably, a —(CH$_2$)$_3$—N($R^{b2}$)$R^{b3}$ group);
$R^{a1}$ represents H or $C_{1-3}$ (e.g. $C_{1-2}$) alkyl (e.g. propyl, such as isopropyl);
$R^{a6}$ and $R^{a7}$ independently represent hydrogen;
$R^{b2}$ and $R^{b3}$ independently represent H or, preferably, $C_{1-4}$ alkyl (such as ethyl or preferably butyl, e.g. n-butyl).

Further preferred compounds of formula I that may be prepared by the process of the invention include those in which:
$R^1$, $R^2$, $R^3$ and $R^4$ independently represent hydrogen or —$NO_2$;
X represents $C_{1-4}$ alkyl (e.g. butyl);
Z represents aryl (e.g. phenyl) optionally substituted by one or more substituents selected from halo (e.g. iodo) and, preferably, —OR$^a$;
$R^a$ represents hydrogen, $C_{1-3}$ alkyl (e.g. methyl) or an oxy-protecting group (e.g. benzyl).

Particularly preferred compounds of formula I that may be prepared by the process of the invention include those in which:
$R^1$, $R^3$ and $R^4$ independently represent hydrogen;
$R^2$ represents —$NO_2$;
X represents n-butyl;
Y represents —C(O)—Z;
Z represents phenyl substituted (e.g. in the ortho- or, preferably, in the para-position) by one or more (e.g. one) substituent(s) selected from —O-benzyl, —OCH$_3$ or, more preferably, —OH.

As stated above, it is preferred that compounds of formula I obtained via the process of the invention are ones in which Y represents —C(O)—Z. Reactions to produce such compounds of formula I (involving reactions of compounds of formula III in which Y represents —C(O)—Z) have the additional advantage that, when 3-aroyl substituted benzofurans are required, a (disadvantageous) Friedel-Crafts acylation step on a 3-unsubstituted benzofuran is circumvented. Further advantages associated with this preferred embodiment of the process of the invention are that compounds of formula I in which Y represents —C(O)—Z may be produced in higher yields as the reaction may proceed in a more regioselective manner than corresponding reactions to produce compounds of formula I in which Y represents H. In this embodiment of the invention, despite the fact that the compound of formula III in which Y represents —C(O)—Z contains two carbonyl moieties, the reaction with the compound of formula II proceeds in a highly regioselective manner, favouring the carbonyl adjacent to (or α- to) the group defined by X (in the initial step condensation reaction between the hydroxylamino moiety of the compound of formula II and the relevant carbonyl group). Surprisingly, this regioselectivity is greater than 90:10 (e.g. 95:5), and selectivities of 99:1 have been achieved.

As stated hereinbefore, it is preferred that compounds of formula I obtained via the process of the invention are ones in which $R^2$ represents —$NO_2$. The formation of compounds of formula I in which $R^2$ is —$NO_2$ normally proceeds via a reaction of a chlorophenyl group with a hydroxy-imine (e.g. 2-hexanone oxime), which is the conventional manner of performing this reaction.

Further, it is also stated above that particularly preferred compounds of formula I obtained via the process of the invention are ones in which Z represents phenyl substituted (e.g. in the para-position) with —OH. When such compounds of the invention are desired and/or required (for example as an intermediate in the synthesis of Dronedarone), it is particularly advantageous that the process of the invention proceeds when the relevant —OH group is unprotected. For instance, processes described in the prior art (e.g. in U.S. Pat. No. 5,223,510, U.S. Pat. No. 5,854,282 and PCT/EP2007/004984), which relate to the Friedel-Crafts acylation of 3-unsubstituted benzofurans, all result in the formation of 3-(4-methoxybenzoyl)benzofurans. Such intermediates may be employed in the synthesis of Dronedarone, but the methoxy group has to be 'deprotected', i.e. the methyl group has to be cleaved from the methyl aryl ether. Such cleavage conditions may also involve metal halide catalysts, such as group III metal halide catalyst, such as $BBr_3$ and $AlCl_3$ (which are disadvantageous in process chemistry for reasons mentioned herein; for example as toxic by-products may be formed, e.g. chloromethane, when $AlCl_3$ is employed). Hence, given that when compounds of formula I in which Z represents phenyl substituted (e.g. in the para-position) with —OH are prepared, such methyl aryl ether cleavage is circumvented, this embodiment of the invention is particularly preferred. Hence, there are several environmental benefits associated with the process of the invention, and particularly with certain embodiments of the process of the invention.

In a further preferred embodiment of the invention, in the process of the invention, a compound of formula II (preferably one as hereinbefore defined), or derivative thereof, is reacted with a compound of formula III in which Y represents —C(O)Z, and Z represents an aryl or heteroaryl group (preferably phenyl) substituted (e.g. in the para-position) by a —$OR^a$ group, in which $R^a$ represents an oxy-protecting group (e.g. benzyl). In this embodiment of the invention, the compound of formula I so formed may be a corresponding one in which $R^a$ also represents the oxy-protecting group (e.g. benzyl) or, preferably, one in which $R^a$ represents hydrogen (i.e. the deprotected occurs during the process of the invention). Hence, this embodiment of the invention may be particularly preferred as, it may reduce the number of overall (separate) process steps that need to be performed. In such an embodiment an inorganic acid, as hereinbefore defined, may be employed in addition to a weak organic acid as hereinbefore defined.

The compounds of formula I obtained by the process of the invention may be separated and/or isolated by standard techniques, for instance by chromatography, crystallisation, evaporation of solvents and/or by filtration.

Advantageously, the process of the invention further comprises the additional step of crystallisation of the compound of formula I from a solution, wherein the solvent is preferably, a non-halogenated solvent. Such a crystallisation may be performed by the addition of a solvent to the reaction mixture of the process of the invention that provides for a compound of formula I (e.g. without prior separation, e.g. isolation, (e.g. by extraction) of the compound of formula I) or, such a crystallisation may be performed after the compound of formula I is separated (e.g. by extraction, optionally followed by removal of solvent) or isolated.

Preferably, the crystallisation mixture/solution (which, in this context, includes a compound of formula I in the reaction mixture after the process of the invention but prior to separation, as well as a compound of formula I that is separated and to which a solvent is then added) is cooled after the addition of the solvent. Conveniently, the mixture is cooled to between about −5 and about 15° C. (for example the optimal temperatures employed are between about +5 and about 15° C.). A preferred 'crystallisation' temperature is about −5° C. (minus five degrees Celsius). The mixture may be cooled using any suitable means, for example ice-baths or cooling systems well known to those skilled in the art and include, for example, heat exchangers.

The 'crystallisation' solvent may also be used to wash the crystallised product, which solvent is preferably pre-cooled. Possible temperatures to which the solvent may be pre-cooled are between about −5° C. to about 5° C. (or, alternatively, the temperature may be between about +5 and about 15° C.). If there is no pre-cooling of the washing solvent, yield may drop. The most preferred temperature is about −5° C.

The 'crystallisation' solvent is preferably a non-halogenated one, e.g. water or it may be an alcohol, such as methanol ethanol, iso-propanol and 1-propanol. The most preferred 'crystallisation' solvent may be methanol. Other preferred crystallisation solvents that may be mentioned include weak organic acids, for example, carboxylic acids (such as butanoic acid, propanoic acid, preferably, formic acid or, more preferably, acetic acid). Such weak organic acids may be mixed with water to form crystallisation co-solvents. When the crystallisation consists of the addition of solvent to a reaction mixture, then that solvent may be water.

It should be appreciated that the purified compound of formula I so formed by the process of the invention may also contain materials other than those specified above.

This product may be further purified using any suitable separation/purification technique or combination of techniques including further crystallisation, distillation, phase separation, adsorption, e.g. using molecular sieves and/or activated carbon, and scrubbing.

In a further aspect of the invention there is provided a process for preparing Dronedarone:

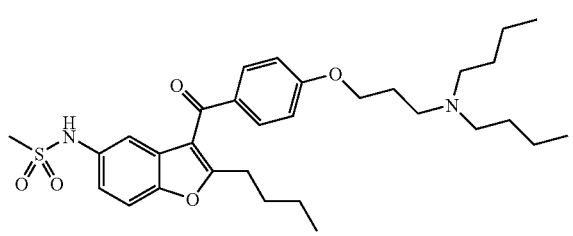 [SMILES: CCCCc1oc2ccc(NS(C)(=O)=O)cc2c1C(=O)c1ccc(OCCCN(CCCC)CCCC)cc1]

(or a salt, e.g. a hydrochloride salt, thereof), which process is characterised in that it includes as a process step a process as described herein (for instance, a process for the preparation of 2-butyl-3-(4-hydroxybenzoyl)-5-nitrobenzofuran or 2-butyl-3-(4-methoxybenzoyl)-5-nitrobenzofuran).

Hence, there is provided a process for the preparation of Dronedarone, or a salt thereof, comprising a process for the preparation of a compound of formula I (e.g. a process for the preparation of 2-butyl-3-(4-hydroxybenzoyl)-5-nitrobenzofuran or 2-butyl-3-(4-methoxybenzoyl)-5-nitrobenzofuran) as described herein, followed by, if necessary/required:

1) if necessary (i.e. in the case of 2-butyl-3-(4-methoxybenzoyl)-5-nitrobenzofuran), conversion of the "4-methoxy" moiety to a "4-hydroxy" moiety (e.g. by cleavage of the methyl phenyl ether moiety under standard conditions, such as by employing $BBr_3$ or $AlCl_3$); and, 2) conversion of the nitro (—$NO_2$) group to a methylsulfonylamino (—$NHS(O)_2CH_3$) group (for example via the conversion of the nitro group to an amino (—$NH_2$) group, followed by reaction with $CH_3$—$S(O)_2$-$L^a$, in which $L^a$ represent halo, and preferably chloro);

3) conversion of the —OH group to the relevant oxy-alkylaminoalkyl (e.g. —O—$(CH_2)_3$—$N(C_4H_9)_2$) group;

4) if necessary/required, conversion of any free base of Dronedarone so formed to a salt (such as a hydrochloride salt).

Such steps are standard steps known to the skilled person, and the steps may be performed in accordance with techniques described in the prior art, such as those references disclosed herein. For example, Dronedarone (or salts thereof) may be prepared from the relevant compounds of formula I using any standard route of synthesising derivatives of benzofuran, such as those described in U.S. Pat. No. 5,223,510. The skilled person will appreciate that the individual steps of the conversions (e.g. those outlined by steps (2) and (3) above) may be performed in any suitable order.

Step (3)

For example, when the compound of formula I is 2-butyl-3-(4-hydroxybenzoyl)-5-nitrobenzofuran, then such a compound may be reacted as set out by step (3) above, which reaction may be performed in the presence of a compound of formula XXV, $$L^{1a1}\text{-}(CH_2)_3\text{—}N(n\text{-butyl})_2 \quad\quad XXV$$

wherein $L^{1a1}$ is a suitable leaving group, such as a sulfonate group (e.g. a triflate or sulfonate), iodo, bromo or, preferably, chloro, under standard alkylation reaction conditions, for example such as those described in U.S. Pat. No. 5,223,510 (see Example 1(e)), to form a Dronedarone intermediate compound of formula XXVI,

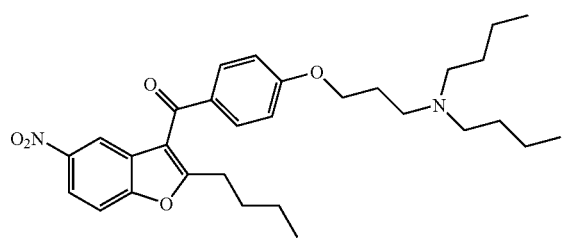

Alternatively, step (3) may be performed in two distinct steps, for example, by reaction of 2-butyl-3-(4-hydroxybenzoyl)-5-nitrobenzofuran with a compound of formula XXVIA, $$L^{1a1}\text{-}(CH_2)_2\text{-}L^{1a1} \quad\quad XXVIA$$

wherein each $L^{1a1}$ independently represents a suitable leaving group, such as iodo, chloro or, preferably, bromo, so forming a Dronedarone intermediate of formula XXVIB,

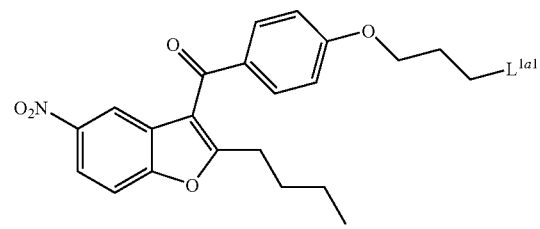

wherein $L^{1a1}$ is as hereinbefore defined (and is preferably bromo), which intermediate may then be reacted with HN(n-butyl)$_2$ (di-n-butylamine) to form a Dronedarone intermediate of formula XXVI, for example under reaction conditions such as those described in Chinese patent publication number CN 101153012).

Step (2)

The intermediate compound of formula XXVI may then be reacted as set out by step (2) above, which may consist of distinct sub-steps:

(i) reduction of the —$NO_2$ group to a —$NH_2$ group, under standard reaction conditions, for example such as those described in U.S. Pat. No. 5,223,510 (see Example 1(f)) or in WO 02/48132, for example hydrogenation in the presence of $H_2$ (e.g. a hydrogen atmosphere or nascent hydrogen, e.g. ammonium formate) and a precious metal catalyst (e.g. $PtO_2$ or Pd/C), in the presence of an appropriate solvent (e.g. an alcohol, e.g. ethanol), thereby forming an intermediate compound of formula XXVI,

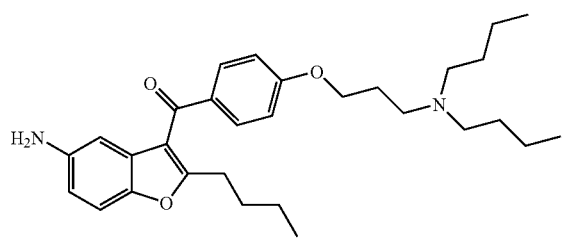

(ii) the Dronedarone intermediate compound of formula XXVII may then be mesylated by reaction with a compound of formula XXVIII, $$H_3C\text{—}S(O)_2\text{-}L^{1a2} \quad\quad XXVIII$$

wherein $L^{1a2}$ represents a suitable leaving group, such as bromo, iodo or, preferably, chloro, under reaction conditions such as those described in U.S. Pat. No. 5,223, 510 (Example 3(a)).

Step (4)

As stated above (step (4)), Dronedarone may be converted into a salt, such as a hydrochloride salt, for example as described in U.S. Pat. No. 5,223,510 (see Example 3(b)), for example by bringing into association Dronedarone and HCl in ether, or as described in U.S. Pat. No. 6,828,448 (see Examples, such as Example 4), for example by bringing into association Dronedarone, hydrochloric acid (e.g. about 30-40%) and an alcoholic solvent, such as isopropanol.

As stated above the above steps may be performed in any feasible order. Hence, 2-butyl-3-(4-hydroxybenzoyl)-5-nitrobenzofuran may first be reacted as set out in step (2), followed by the reaction(s) as set out in step (3). The preparation of Dronedarone may therefore proceed via the following intermediate compounds of formulae XXIX and XXX (step 2),

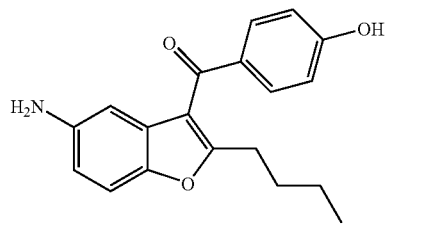

XXIX

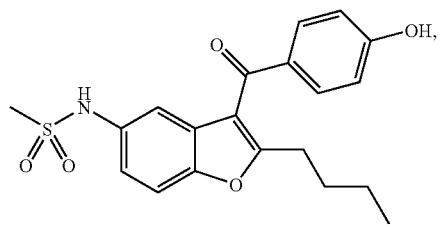

XXX and, may also proceed via the intermediate compound of formula XXXI (step (3), when performed as a two-two process),

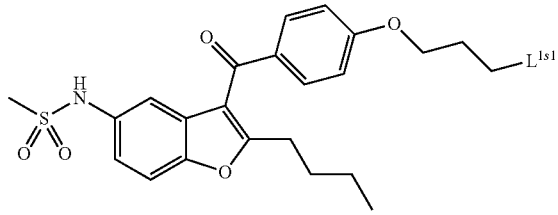

XXXI wherein $L^{1a1}$ is as hereinbefore defined.

The skilled person will appreciate that the intermediate compounds of formulae XXVI, XXVIB, XXVII, XXIX, XXX and XXXI may also be compounds of formula I. Hence, the conversion of such compounds of formula I (which may be prepared directly from the process of the invention) may not require all of the process steps (or sub-process steps) outlined above (i.e. steps (1), (2), (3) and (4)) in order to provide Dronedarone, or a salt (e.g. a HCl salt) thereof. In such instance, it is immediately clear to the skilled person which of the above-mentioned steps are required for the appropriate conversions.

There is further provided a process for the preparation of an intermediate of Dronedarone (or a salt thereof, e.g. a hydrochloride salt), which process comprises a process step as hereinbefore described followed by one or more process steps that lead to the formation of Dronedarone, or a salt thereof. For example, such further process steps may include the step (1) outlined above (if necessary/required) and/or any one or more of the process steps disclosed in steps (2), (3) and (4) above, in any feasible order (thereby forming an intermediate of formula XXVI, XXVIB, XXVII, XXIX, XXX or XXXI). The skilled person will appreciate that steps (2), (3) and (4) above may each require multiple separate reaction steps for the relevant conversion to be effected.

The processes described herein may be operated as a batch process or operated as a continuous process and may be conducted on any scale.

In general, the processes described herein, may have the advantage that the compounds of formula I may be produced in a manner that utilises fewer reagents and/or solvents, and/or requires fewer reaction steps (e.g. distinct/separate reaction steps) compared to processes disclosed in the prior art.

The process of the invention may also have the advantage that the compound of formula I is produced in higher yield, in higher purity, in higher selectivity (e.g. higher regioselectivity), in less time, in a more convenient (i.e. easy to handle) form, from more convenient (i.e. easy to handle) precursors, at a lower cost and/or with less usage and/or wastage of materials (including reagents and solvents) compared to the procedures disclosed in the prior art. Furthermore, there may be several environmental benefits of the process of the invention, such as the circumvention of the use of halogenated solvents (e.g. when avoiding the need to perform a Friedel-Crafts reaction or a deprotection of e.g. a —$OCH_3$ group, which may be required for certain steps performed by processes in the prior art, to a —OH group).

In further embodiments, the present invention is:

1. A process for the preparation of a compound of formula I,

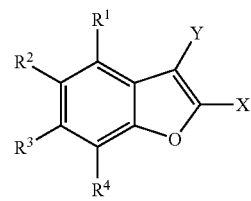

I wherein $R^1$, $R^2$, $R^3$ and $R^4$ independently represent hydrogen, halo, —$NO_2$, —CN, —$C(O)_2R^{x1}$, —$OR^{x2}$, —$SR^{x3}$, —$S(O)R^{x4}$, —$S(O)_2R^{x5}$, —$N(R^{x6})R^{x7}$, —$N(R^{x8})C(O)R^{x9}$, —$N(R^{x10})S(O)_2R^{x11}$ or $R^{x12}$;

X represents hydrogen or $C_{1-6}$ alkyl optionally substituted by one or more halo atoms;

Y represents —C(O)—Z;

Z represents aryl or heteroaryl, both of which are optionally substituted by one or more substituents selected from —$OR^a$, halo, —$NO_2$, —CN, —$C(O)_2R^{a1}$, —$SR^{a3}$, —$S(O)R^{a4}$, —$S(O)_2R^{a5}$, —$N(R^{a6})R^{a7}$, —$N(R^{a8})C(O)R^{a9}$, —$N(R^{a10})S(O)_2R^{a11}$ and $R^{a12}$;

$R^a$ represents an oxy-protecting group, hydrogen or $C_{1-6}$ alkyl optionally substituted by one or more substituents selected from halo, $-C(O)_2R^{b1}$ and $-N(R^{b2})R^{b3}$;
$R^{x1}, R^{x2}, R^{x3}, R^{x6}, R^{x7}, R^{x8}, R^{x9}, R^{x10}, R^{a1}, R^{a3}, R^{a6}, R^{a7}, R^{a8}, R^{a9}, R^{a10}, R^{b1}, R^{b2}$ and $R^{b3}$ independently represent hydrogen or $C_{1-6}$ alkyl optionally substituted by one or more halo atoms;
$R^{x4}, R^{x5}, R^{x11}, R^{x12}, R^{a4}, R^{a5}, R^{a11}$ and $R^{a12}$ independently represent $C_{1-6}$ alkyl optionally substituted by one or more halo atoms;
which process comprises reaction of a compound of formula II,

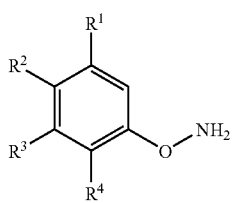

II or a protected derivative or salt thereof, wherein $R^1$, $R^2$, $R^3$, $R^4$ are as defined above, with a compound of formula III,

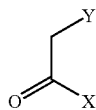

III wherein Y and X are as defined above.

2. The process for the preparation of a compound of formula I as defined in embodiment 1, but in which Y represents H or $-C(O)Z$,
which process comprises reaction of a compound of formula II as defined in embodiment 1, or a protected derivative or salt thereof, with
a compound of formula III as defined in embodiment 1, but in which but in which Y represents H or $-C(O)Z$,
characterised in that the reaction is performed as a "one-pot" procedure.

3. A process for the preparation of a compound of formula I as defined in embodiment 1, but in which Y represents H or $-C(O)Z$, and characterised in that $R^2$ represents $-NO_2$,
which process comprises reaction of a compound of formula II as defined in embodiment 1, or a protected derivative or salt thereof, but in which $R^2$ represents $-NO_2$, with
a compound of formula III as defined in embodiment 1, but in which Y represents H or $-C(O)Z$.

4. A process for the preparation of a compound of formula I as defined in embodiment 1, but in which Y represents H or $-C(O)Z$,
which process comprises reaction of a compound of formula II as defined in embodiment 1, or a protected derivative or salt thereof, with
a compound of formula III as defined in embodiment 1, but in which but in which Y represents H or $-C(O)Z$,
characterised in that the process is performed in the absence of an acylating reagent.

5. A process as defined in any one of embodiments 1, 2 or 4, wherein $R^2$ represents $-NO_2$.

6. A process as defined in any one of embodiments 2, 3 or 4, wherein Y represents $-C(O)-Z$.

7. A process as defined in any one of embodiments 1, 3 or 4, wherein the reaction is performed as a "one-pot" procedure.

8. A process as defined in any one of embodiments 1, 2 or 3, wherein the reaction is performed in the absence of an acylating reagent.

9. A process as defined in any one of the preceding embodiments, wherein $R^1$, $R^3$ and $R^4$ represent hydrogen.

10. A process as defined in any one of the preceding embodiments, wherein X represents n-butyl.

11. A process as defined in any one of the preceding embodiments, wherein Z represents phenyl substituted in the para-position by $-OH$, $-OCH_3$ or $-O$-benzyl.

12. A process as defined in any one of the preceding embodiments, wherein the reaction is performed in the presence of an acid.

13. A process as defined in embodiment 12, wherein the acid is a weak organic acid.

14. A process as defined in embodiment 13, wherein the concentration of the compound of formula II in the weak organic acid solvent is from about 0.1 M to about 5 M.

15. A process as defined in embodiment 14, wherein the concentration is between about 0.6 M and 1.5 M.

16. A process as defined in any one of the preceding embodiments, wherein the compound of formula II is added to the compound of formula III.

17. A process as defined in any one of the preceding embodiments, wherein the reaction is performed at elevated temperature.

18. A process as defined in any one of the preceding embodiments, wherein the presence of compounds of formulae II and III are in a molar ratio of from about 3:2 to about 2:3.

19. A process as defined in any one of the preceding embodiments, wherein the process proceeds via an intermediate of formula XXIV,

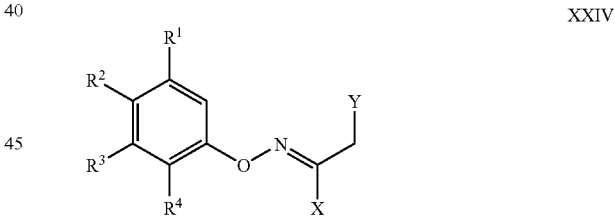

XXIV in which Y represents $-C(O)Z$, and $R^1$, $R^2$, $R^3$, $R^4$, X and Z are as defined in any one of embodiments 1, 3, 9, 10 or 11.

20. A process as defined in any one of the preceding embodiments, wherein the process further comprises the additional step of crystallisation of the compound of formula I from a solution.

21. A process for preparing Dronedarone, or a salt thereof, which process is characterised in that it includes as a process step a process as defined in any one of embodiments 1 to 20.

22. A process for preparing a pharmaceutical formulation comprising Dronedarone, or a salt thereof, which process is characterised in that it includes as a process step a process as defined in any one of embodiments 1 to 20.

23. A process for the preparation of Dronedarone, or a salt thereof, as defined in embodiment 21, which comprises:
1) a process for the preparation of 2-butyl-3-(4-hydroxybenzoyl)-5-nitrobenzofuran or 2-butyl-3-(4-methoxybenzoyl)-

5-nitrobenzofuran as claimed in any one of embodiments 1 to 20;

2) in the case of 2-butyl-3-(4-methoxybenzoyl)-5-nitrobenzofuran), conversion of the 4-methoxy moiety to a 4-hydroxy moiety; followed by, in any feasible order, 3) conversion of the nitro (—NO$_2$) group to a methylsulfonylamino (—NHS(O)$_2$CH$_3$) group;

4) conversion of the —OH group to the —O—(CH$_2$)$_3$—N(C$_4$H$_9$)$_2$ group; and 5) if necessary/required, conversion of any free base of Dronedarone so formed to a salt.

24. A process as claimed in embodiment 23, wherein step (1) comprises the preparation of 2-butyl-3-(4-hydroxybenzoyl)-5-nitrobenzofuran, which is followed by step (4), then step (3), then step (5).

25. A process for the preparation of a pharmaceutical formulation comprising Dronedarone, or a salt thereof, which process comprises a process for the preparation of Dronedarone, or, a salt thereof, as defined in embodiment 21, 23 or 24, followed by bringing into association Dronedarone (or a salt thereof) so formed, with (a) pharmaceutically-acceptable excipient(s), adjuvant(s), diluent(s) or carrier(s).

26. A process for the preparation of a pharmaceutical formulation comprising Dronedarone, or a salt thereof, which process comprises a process for the preparation of Dronedarone, or, a salt thereof, as defined in embodiment 21, 23 or 24, followed by bringing into association Dronedarone (or a salt thereof), with a pharmaceutically acceptable non-ionic hydrophilic surfactant selected from poloxamers, and, optionally, one or more pharmaceutical excipients.

27. A process for the preparation of an intermediate of Dronedarone, or a salt thereof, which process comprises a process step as defined in any one of embodiments 1 to 20, followed by any one or more process steps disclosed in (1), (2), (3) and (4) described in embodiment 23.

28. A process for the preparation of a compound of formula II, as defined in embodiment 1, which comprises reaction of a compound of formula IV,

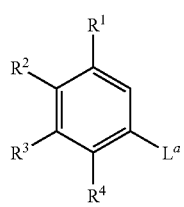
IV wherein L$^a$ represents a suitable leaving group, and R$^1$, R$^2$, R$^3$ and R$^4$ are as defined in claim 1, with a compound of formula V,

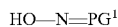
HO—N=PG$^1$  V wherein PG$^1$ represents an imino-protecting group, or a compound of formula VI,

HO—N(H)—PG$^2$  VI wherein PG$^2$ represents an amino protecting group, to form a compound of formula IIA or IIB,

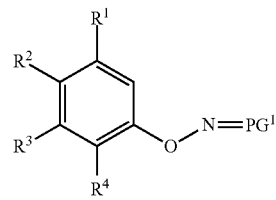
IIA

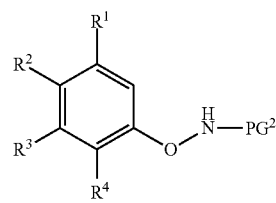
IIB respectively, followed by deprotection.

29. A compound of formula III, as defined in embodiment 1, but in which:
Y represents —C(O)—Z;
X represents n-butyl; and
Z is as defined in embodiment 1 or embodiment 11.

30. A process for the preparation of a compound of formula III, as defined in embodiment 1, but in which Y represents —C(O)Z, which process comprises:
(i) reaction of a compound of formula VII,

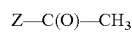
Z—C(O)—CH$_3$  VII wherein Z is as defined in embodiment 1, with a compound of formula VIII,

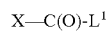
X—C(O)-L$^1$  VIII wherein L$^1$ represents a suitable leaving group;
(ii) reaction of a compound of formula IX,

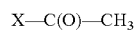
X—C(O)—CH$_3$  IX wherein X is as defined in embodiment 1, with a compound of formula X,

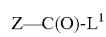
Z—C(O)-L$^1$  X wherein Z is as defined in embodiment 1, and L$^1$ is as defined above;
(iii) for compounds of formula III, in which Z represents aryl or heteroaryl substituted by —OH, reaction of a corresponding compound of formula XI,

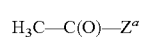
H$_3$C—C(O)—Z$^a$  XI wherein Z$^a$ represents aryl or heteroaryl substituted with —O—C(O)—X (in which X is as defined in embodiment 1), with base;
(iv) decarboxylation of a compound of formula XII,

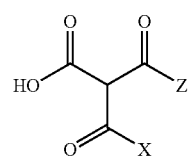
XII or a protected derivative thereof, wherein X and Z are as defined in embodiment 1;

(v) hydrolysis of a compound of formula XIII,

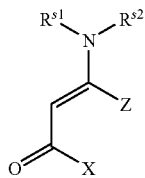

wherein $R^{s1}$ and $R^{s2}$ independently represent hydrogen, $C_{1-6}$ alkyl optionally substituted by one or more halo atoms, or $R^{s1}$ and $R^{s2}$ are linked together to form, together with the nitrogen atom to which they are necessarily attached, a 4- to 8-membered heterocycloalkyl group, and X and Z are as defined in embodiment 1;

(vi) reaction of a compound of formula XIV,

    XIV wherein Z is as defined in embodiment 1, with either:
(A) a compound of formula XV,

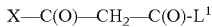    XV or a protected derivative thereof, wherein X is as defined in embodiment 1, and $L^1$ is as defined above; or
(B) a compound of formula XVI,

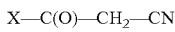    XVI or a protected derivative thereof, wherein X is as defined in embodiment 1;

(vii) reduction of a compound of formula XVIA,

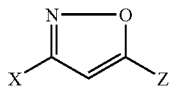    XVIA or a compound of formula XVIB,

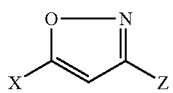    XVIB wherein (in both cases) X and Z are as defined in embodiment 1, in the presence of aqueous acid.

The following examples are merely illustrative examples of the processes of the invention described herein.

All equipment, reagents and solvents used were standard laboratory equipment, e.g. glassware, heating apparatus and HPLC apparatus.

EXAMPLE A

Example 1

2-Butyl-3-(4-hydroxybenzoyl)-5-nitrobenzofuran (a) 4-Benzyloxy acetophenone (10 g) and ethyl pentanoate (1.2 equiv.) were dissolved in toluene (30 g) containing DMF (6.5 g). The mixture was heated to 65° C. and NaOMe (3 eq) was added in portions over 3.5 h. Analysis of a sample withdrawn after 4 h showed a conversion of 97%. The reaction mixture was quenched by addition to water (30 ml). This was proceeded by acidification with hydrochloric acid and extraction with toluene (40 ml), followed by solvent change to MeOH (100 ml). The product, which crystallises upon cooling, was collected by filtration, washed with methanol and dried under vacuum. Yield 8.04 g of 1-(4-benzyloxyphenyl)-heptane-1,3-dione.

(b) 1-(4-Benzyloxyphenyl)-heptane-1,3-dione (4 g; see step (a) above) was dissolved in toluene (20 ml) and Pd/C (3%; 80 mg) was added. The mixture was stirred at room temperature until hydrogen uptake ceased. After filtration of the catalyst, the solvent was evaporated leaving 2.84 g, 100%, 1-(4-hydroxyphenyl)-heptane-1,3-dione.

(c) O-4-nitrophenylhydroxylamine (1.0 g), was suspended in acetic acid (10 ml) and 1-(4-hydroxyphenyl)-heptane-1,3-dione (1.36 g; see step (b) above) was added. The mixture was stirred for 3 h at 70° C. and then at 100° C. for an additional 22 h. The mixture was cooled to room temperature and the solvent evaporated under vacuum. Yield 80% of 2-Butyl-3-(4-hydroxybenzoyl)-5-nitrobenzofuran.

Example 2

2-Butyl-3-(4-hydroxybenzoyl)-5-nitrobenzofuran 1-(4-Benzyloxyphenyl)-heptane-1,3-dione (191 mg; see Example 1 (a)), was suspended in 1 ml HBr/acetic acid and O-4-nitrophenylhydroxylamine, 100 mg, was added. The mixture was stirred at room temperature for 6 h. After quenching with water and extraction to EtOAc followed by evaporation of the solvent, a crude material containing approximately 125 mg of the title compound was obtained. Yield ca. 59%.

Example 3

2-Butyl-3-(4-methoxybenzoyl)-5-nitrobenzofuran

O-4-nitrophenylhydroxylamine (100 mg), was suspended in 0.5 ml acetic acid and 1-(4-methoxyphenyl)-heptane-1,3-dione was added. The mixture was stirred at 70° C. for 3 h and then at 100° C. for an additional 14 h. The mixture was cooled to room temperature and the solvent evaporated under vacuum. Yield 70% of 2-butyl-3-(4-methoxybenzoyl)-5-nitrobenzofuran.

Example 4

Synthesis of Dronedarone

Dronedarone is synthesised using standard synthetic processes described in the prior art (and referenced herein) incorporating any of the processes described herein, for example the processes to the intermediates 2-butyl-3-(4-hydroxybenzoyl)-5-nitrobenzofuran and 2-butyl-3-(4-methoxybenzoyl)-5-nitrobenzofuran described in Example A (Examples 1 to 3 above). Dronedarone can be made from these intermediates using any standard routes for converting a nitro (—$NO_2$) group to a methylsulfonylamino (—$NHS(O)_2CH_3$) group (for example via an amino (—$NH_2$) group) and converting a —OH (or —$OCH_3$) group to any relevant oxy-alkylaminoalkyl (e.g. —O—$(CH_2)_3$—$N(C_4H_9)_2$) group. Further, salts (such as hydrochloride salts) of the relevant compounds may also be prepared. Such steps are standard steps known to the skilled person, and the steps may be performed in accordance with techniques described in the prior art, such as those references disclosed herein.

EXAMPLE B

Example 1

Ethyl N-(4-nitrophenoxy)acetimidate

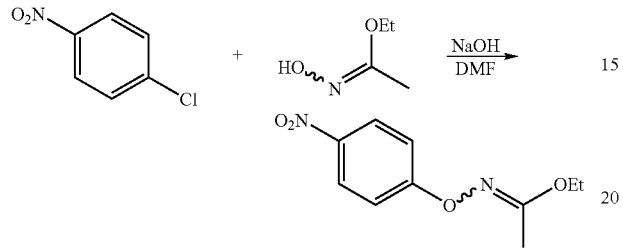

4-Chloronitrobenzene, 136.2 g, and 111.4 g ethyl N-hydroxyacetimidate are dissolved in 216 ml DMF. The temperature is adjusted to 30° C. and 41.6 g solid NaOH is added in 8 portions keeping the temperature at 30-35° C. After one hour the temperature is adjusted to 40-45° C. and the mixture stirred for 1.5 hours. Cooling is applied and 520 ml water is fed at such a rate as to keep the temperature at ca 40° C. The slurry formed is cooled to 17° C. and filtered. The filter cake is washed with 175 ml ethanol/water 90/10 (V/V) followed by 175 ml water. Wet product, 214.5 g, corresponding to 192 g dry ethyl N-(4-nitrophenoxy)acetimidate is isolated. Yield 98.5%.

Example 2

Ethyl N-(4-nitrophenoxy)acetimidate

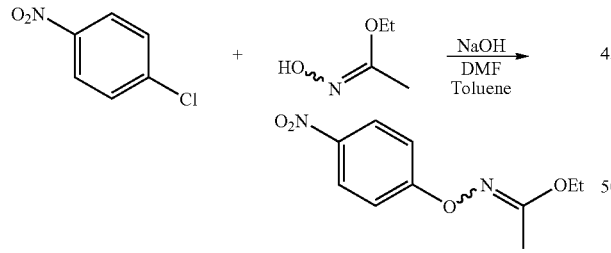

To a solution of 549 g ethyl N-hydroxy acetimidate in 976 g toluene is added 1267 g DMF, 39.9 g Aliquat 336 and 799 g 4-chloronitrobenzene. The temperature is adjusted to 30° C. and 223 g solid NaOH is added in portions of 25-30 g every 10-15 minutes. When addition is complete, the jacket temperature is set to 40° C. and the mixture stirred until reaction is complete, 3-4 h. The jacket temperature is adjusted to 50° C. and ca 80% of the toluene stripped at reduced pressure. 3040 g Water is added keeping the temperature at max 45° C. The formed slurry is efficiently agitated and the residual toluene stripped at reduced pressure. After cooling to 15° C. the product is filtered and washed with 1080 g EtOH/water 90/10 (V/V) followed by 1080 g water. Wet product, 1188 g, corresponding to 1080 g dry ethyl N-(4-nitrophenoxy)acetimidate is obtained. Yield 95%.

Example 3

O-(4-Nitrophenyl)hydroxylamine

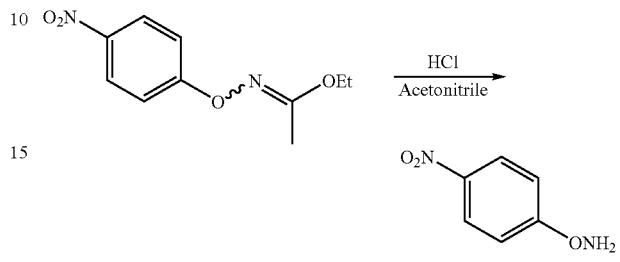

Wet ethyl N-(4-nitrophenoxy)acetimidate, 781 g (dry weight) is dissolved in 2100 g acetonitrile and the temperature adjusted to ca 25° C. 515 g 37% hydrochloric acid is added at such rate as to keep the temperature below 30° C. The mixture is stirred at 25-30° C. until the reaction is complete, ca 2 h. Then 2090 g of 12% NaOH(aq) is added at 25-30° C. and the mixture stirred for ca 30 minutes. Vacuum is applied and ca 85% of the acetonitrile stripped at 100 mbar and a jacket temperature of 50° C. (inner temperature 25-30° C.). Water, 2090 g, is added and the slurry stirred for 60 minutes. The product is filtered and washed with 505 g water followed by drying under vacuum at 40° C. O-(4-Nitrophenyl)hydroxylamine, 560 g, is obtained. Yield 94%.

Example 4

1-(4-Hydroxyphenyl)-1,3-heptandione

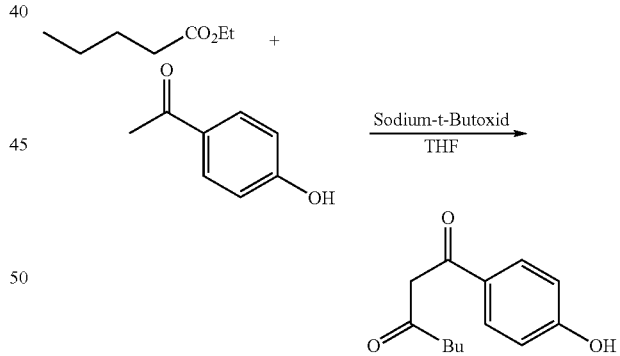

Sodium tert-butoxide, 1270 g, is slurried in 1390 g THF and the mixture heated to reflux temperature. A solution of 580 g 4-hydroxyacetophenone and 555 g ethylvalerate in 1390 g THF is added over 30 minutes. The solution is stirred at reflux temperature until the reaction is complete, ca 4.5 h, and then quenched by addition of the reaction mixture to 1270 g 37% HCl. The mixture is concentrated by distillation of THF at reduced pressure and to the residue is added 900 g toluene. The water phase is separated and the toluene phase washed with 900 g 10% aqueous NaCl. The toluene is stripped at reduced pressure and the residual oil diluted with 850 g acetic acid. The solution is cooled to 8° C. and 850 ml water added slowly. The formed slurry is stirred at 5-8° C. for 90 minutes and then filtered and washed with 608 g 20% aqueous acetic acid. Drying under vacuum at 40° C. gives 608 g 1-(4-hydroxyphenyl)-1,3-heptandione.

Yield 65%

Example 5

2-Butyl-3-(4-hydroxybenzoyl)-5-nitrobenzofuran

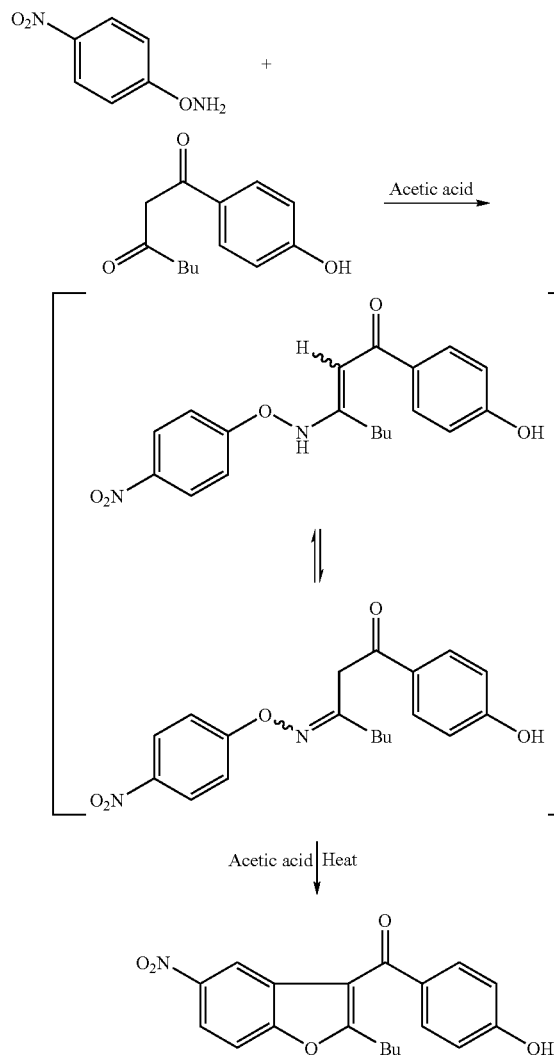

1-(4-hydroxyphenyl)-1,3-heptandione, 697 g, is dissolved in 2532 g acetic acid. O-(4-Nitrophenyl)hydroxylamine, 488 g, is added in portions at ca 20° C. The formed slurry is diluted with 739 g acetic acid and the mixture heated to 115° C. and stirred for 3 h. The dark solution is cooled and 1635 g water is added keeping the temperature at 70-80° C. The temperature is adjusted to 60° C. and seeding crystals are added. When crystallisation has started, the slurry is cooled to 4° C., filtered and washed with 870 g of 67% aqueous acetic acid followed by 580 g water. Drying at reduced pressure at 70° C. gives 736 g 2-butyl-3-(4-hydroxybenzoyl)-5-nitrobenzofuran. Yield 69%.

Example 6

1-(4-Hydroxyphenyl)heptane-1,3-dione-3-[O-(4-nitrophenyl) oxime]

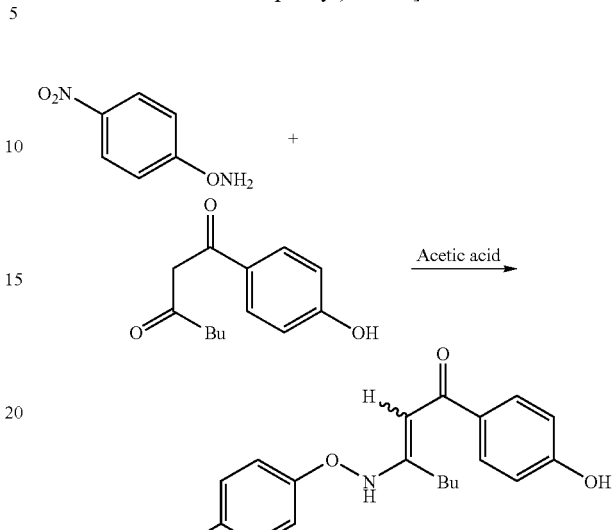

1-(4-Hydroxyphenyl)-1,3-heptandione, 1121 g, is dissolved in 4070 g acetic acid. O-(4-Nitrophenyl)hydroxylamine, 784 g, is added in portions keeping the temperature at ca 20° C. The formed slurry is stirred for 3 h, cooled to 15° C., filtered and washed with 1590 g acetic acid. 1944 g wet cake corresponding to 1596 g dry 1-(4-hydroxyphenyl)heptane-1,3-dione-3-[O-(4-nitrophenyl)oxime] is obtained. Yield 88%.

Example 7

2-Butyl-3-(4-hydroxybenzoyl)-5-nitrobenzofuran

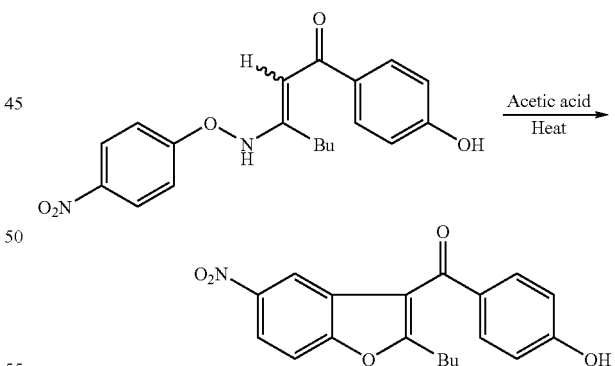

The wet 1-(4-hydroxyphenyl)heptane-1,3-dione-3-[O-(4-nitrophenyl)oxime], 1944 g, obtained in example 6 is slurried in 4900 g acetic acid. The slurry is heated to 115° C. and stirred for 3 h. The dark solution formed is cooled and 2630 g water is added keeping the temperature at 70-80° C. The temperature is adjusted to 60° C. and seeding crystals are added. When crystallisation has started, the slurry is cooled to 4° C., filtered and washed with 1400 g of 67% aqueous acetic acid followed by 930 g water. Drying at reduced pressure at 70° C. gives 1182 g 2-butyl-3-(4-hydroxybenzoyl)-5-nitrobenzofuran. Yield 78%.

Example 8

Synthesis of Dronedarone

Dronedarone is synthesised using standard synthetic processes described in the prior art (and referenced herein) incorporating any of the processes described herein, for example the processes to the intermediates 2-butyl-3-(4-hydroxybenzoyl)-5-nitrobenzofuran and 2-butyl-3-(4-methoxybenzoyl)-5-nitrobenzofuran described in Example B above (examples 1 to 7). Dronedarone can be made from these intermediates using any standard routes for converting a nitro (—NO₂) group to a methylsulfonylamino (—NHS(O)₂CH₃) group (for example via an amino (—NH₂) group) and converting a —OH (or —OCH₃) group to any relevant oxy-alkylaminoalkyl (e.g. —O—(CH₂)₃—N(C₄H₉)₂) group. Further, salts (such as hydrochloride salts) of the relevant compounds may also be prepared. Such steps are standard steps known to the skilled person, and the steps may be performed in accordance with techniques described in the prior art, such as those references disclosed herein.

EXAMPLE C

Dronedarone may be formulated into a pharmaceutically acceptable formulation using standard procedures, for example to form the product marketed under the brand name, Multaq®.

For example, there is provided a process for preparing a pharmaceutical formulation comprising Dronedarone, or a salt thereof (e.g. a hydrochloride salt), which process is characterised in that it includes as a process step a process as hereinbefore defined. The skilled person will know what such pharmaceutical formulations will comprise/consist of (e.g. a mixture of active ingredient (i.e. Dronedarone or a salt thereof) and pharmaceutically acceptable excipient, adjuvant, diluent and/or carrier).

There is further provided a process for the preparation of a pharmaceutical formulation comprising Dronedarone (or a salt thereof, e.g. a hydrochloride salt; which formulation may be Multaq®), which process comprises bringing into association Dronedarone, or a pharmaceutically acceptable salt thereof (which may be formed by a process as hereinbefore described), with (a) pharmaceutically acceptable excipient(s), adjuvant(s), diluent(s) and/or carrier(s).

There is further provided a process for the preparation of a pharmaceutical formulation comprising Dronedarone (or a salt thereof, e.g. a hydrochloride salt) as described in the art (for example in U.S. Pat. No. 5,985,915 (see Example 3), US 2004/0044070 (see Examples 1 to 5), U.S. Pat. No. 7,323,439, US 2008/0139645 and/or CN 101152154), which process comprises bringing into association Dronedarone (or a salt thereof, e.g. a hydrochloride salt), with the other ingredients of the relevant formulations. For example, Dronedarone hydrochloride may be brought into association with: maize starch, talc, anhydrous colloidal silica, magnesium stearate and lactose (see Example 3 of U.S. Pat. No. 5,985, 915); mannitol, anhydrous sodium dihydrogen phosphate and, optionally, water (see Example 5 of U.S. Pat. No. 5,985, 915); hydroxypropyl-β-cyclodextrin, monosodium phosphate dehydrate and mannitol (see Example 1 of US 2004/0044070); hydroxypropyl-β-cyclodextrin, anhydrous sodium dihydrogen phosphate, mannitol and, optionally, water (see Examples 2 and 3 of US 2004/0044070); mixture of methylated derivatives of β-cyclodextrin, mannitol and, optionally, water (see Example 4 of US 2004/0044070). The formulations described may be oral tablet forms or injectable forms (e.g. US 2004/0044070 may describe injectable forms).

In particular, there may be further provided a process for the preparation of a pharmaceutical formulation, comprising bringing into association Dronedarone (or a salt thereof; prepared in accordance with the processes described herein), with a pharmaceutically acceptable non-ionic hydrophilic surfactant selected from poloxamers (e.g. poloxamer 407; Synperonic® PE/F127), optionally in combination with one or more pharmaceutical excipients, for example as described in U.S. Pat. No. 7,323,493. For example, Dronedarone hydrochloride may be brought into association with: methylhydroxypropylcellulose, lactose monohydrate, modified corn starch, polyvinylpyrrolidone, Synperonic® PE/F127 and, optionally, any one or more of anhydrous colloidal silica, magnesium stearate and water (see e.g. Tablet A and Examples 1 to 3 of U.S. Pat. No. 7,323,493); modified corn starch, lactose monohydrate, talc, anhydrous colloidal silica and magnesium stearate (see e.g. gelatin capsule of U.S. Pat. No. 7,323,493); microcrystalline cellulose, anhydrous colloidal silica, anhydrous lactose, polyvinylpyrrolidone, Synperonic® PE/F127 and, optionally, one or more of macrogol 6000 and magnesium stearate (see Examples 4 to 6 of U.S. Pat. No. 7,323,493); microcrystalline cellulose, corn starch, polyvinylpyrrolidone, Synperonic® PE/F127, anhydrous colloidal silica, magnesium stearate and lactose monohydrate (see Examples 7 and 8 of U.S. Pat. No. 7,323,493). The skilled person will appreciate that for example in the above-mentioned list of ingredients, every single ingredient need not be present in the formulation (and hence, the process for preparing the formulation may comprise bringing Dronedarone into association with only some of the ingredients mentioned above). Further, where an ingredient is mentioned, the skilled person will appreciate that it may be replaced by another equivalent or similar ingredient that serves the same function (for example Synperonic® PE/F127 may be replaced by another suitable surfactant and methylhydroxypropylcellulose and corn starch may be replaced by another ingredient, such as a suitable disintegrating agent or bioadhesion promoting agent, etc).

When a pharmaceutical formulation is referred to herein, it includes a formulation in an appropriate dosage form for intake (e.g. in a tablet form or an injectable form). Hence, any process mentioned herein that relates to a process for the preparation of a pharmaceutical formulation comprising Dronedarone, or a salt thereof, may further comprise an appropriate conversion to the appropriate dosage form (and/or appropriate packaging of the dosage form). For example U.S. Pat. No. 7,323,493 may describe processed to an appropriate tablet form (see Examples 1 to 8), which may be a gelatin capsule.

The invention claimed is:

1. A process for the preparation of a compound of formula I, or a salt thereof

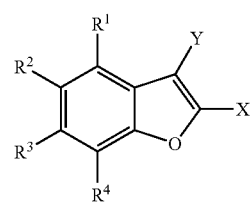

I wherein $R^1$, $R^2$, $R^3$ and $R^4$ independently represent hydrogen, halo, —$NO_2$, —CN, —$C(O)_2R^{x1}$, —$OR^{x2}$, —$SR^{x3}$, —$S(O)R^{x4}$, —$S(O)_2R^{x5}$, —$N(R^{x6})R^{x7}$, —$N(R^{x8})C(O)R^{x9}$, —$N(R^{x10})S(O)_2R^{x11}$ or $R^{x12}$;

X represents hydrogen or $C_{1-6}$ alkyl optionally substituted by one or more halo atoms;

Y represents —C(O)—Z;

Z represents aryl or heteroaryl, both of which are optionally substituted by one or more substituents selected from —$OR^a$, halo, —$NO_2$, —CN, —$C(O)_2R^{a1}$, —$SR^{a3}$, —$S(O)R^{a4}$, —$S(O)_2R^{a5}$, —$N(R^{a6})R^{a7}$, —$N(R^{a8})C(O)R^{a9}$, —$N(R^{a10})S(O)_2R^{a11}$ and $R^{a12}$;

$R^a$ represents an oxy-protecting group, hydrogen or $C_{1-6}$ alkyl optionally substituted by one or more substituents selected from halo, —$C(O)_2R^{b1}$ and —$N(R^{b2})R^{b3}$;

$R^{x1}$, $R^{x2}$, $R^{x3}$, $R^{x6}$, $R^{x7}$, $R^{x8}$, $R^{x9}$, $R^{x10}$, $R^{a1}$, $R^{a3}$, $R^{a6}$, $R^{a7}$, $R^{a8}$, $R^{a9}$, $R^{a10}$, $R^{b1}$, $R^{b2}$ and $R^{b3}$ independently represent hydrogen or $C_{1-6}$ alkyl optionally substituted by one or more halo atoms;

$R^{x4}$, $R^{x5}$, $R^{x11}$, $R^{x12}$, $R^{a4}$, $R^{a5}$, $R^{a11}$ and $R^{a12}$ independently represent $C_{1-6}$ alkyl optionally substituted by one or more halo atoms;

which process comprises reaction of a compound of formula II,

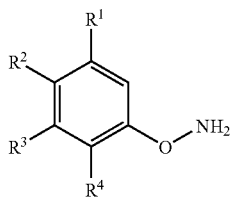

II or a protected derivative or salt thereof, wherein $R^1$, $R^2$, $R^3$, $R^4$ are as defined above, with a compound of formula III, or a salt thereof without acylation

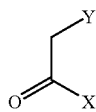

III wherein Y and X are as defined above.

2. A process as claimed in claim 1, wherein $R^2$ represents —$NO_2$.

3. A process as claimed in claim 1, wherein the reaction is performed as a "one-pot" procedure.

4. A process as claimed in claim 1, wherein $R^1$, $R^3$ and $R^4$ represent hydrogen.

5. A process as claimed in claim 1, wherein X represents n-butyl.

6. A process as claimed in claim 1, wherein Z represents phenyl substituted in the para-position by —OH, —$OCH_3$ or —O-benzyl.

7. A process as claimed in claim 1, wherein the reaction is performed in the presence of an acid.

8. A process as claimed in claim 7, wherein the reaction is performed in the presence of a weak organic acid.

9. A process as claimed in claim 8, wherein the compound of formula II has a concentration in the weak organic acid from about 0.1 M to about 5 M.

10. A process as claimed in claim 9, wherein the compound of formula II has a concentration in the weak organic acid between about 0.6 M and 1.5 M.

11. A process as claimed in claim 1, wherein the compound of formula II is added to the compound of formula III.

12. A process as claimed in claim 1, wherein the reaction is performed at elevated temperature.

13. A process as claimed in claim 1, wherein the presence of compounds of formulae II and III are in a molar ratio of (compound of formula II:compound of formula III) from about 3:2 to about 2:3.

14. A process as claimed in claim 1, wherein the process proceeds via an intermediate of formula XXIV,

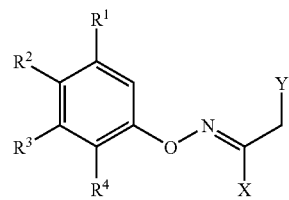

XXIV in which Y represents —C(O)Z, and $R^1$, $R^2$, $R^3$, $R^4$, X and Z are as defined in any one of claims 1, 4, 5 or 6.

15. A process as claimed in claim 1, wherein the process further comprises the additional step of crystallisation of the compound of formula I from a solution.

16. An improved process for preparing Dronedarone, or a salt thereof, wherein the improvement comprises employing a process as claimed in claim 1.

17. A process for preparing a pharmaceutical formulation comprising Dronedarone, or salt thereof which comprises employing a process of claim 1 and combining the Dronedarone, or salt thereof with a pharmaceutical career or diluent.

18. A process for the preparation of Dronedarone, or a salt thereof, which comprises:
1) preparing 2-butyl-3-(4-hydroxybenzoyl)-5-nitrobenzofuran or 2-butyl-3-(4-methoxybenzoyl)-5-nitrobenzofuran using the process of claim 1;
2) in the case of 2-butyl-3-(4-methoxybenzoyl)-5-nitrobenzofuran), converting the 4-methoxy moiety to a 4-hydroxy moiety; followed by, in any feasible order,
3) converting the nitro (—$NO_2$) group to a methylsulfonylamino (—$NHS(O)_2CH_3$) group;
4) converting the —OH group to the —O—$(CH_2)_3$—N$(C_4H_9)_2$ group; and
5) if necessary/required, converting any free base of Dronedarone so formed to a salt.

19. A process as claimed in claim 18, wherein step (1) comprises the preparation of 2-butyl-3-(4-hydroxybenzoyl)-5-nitrobenzofuran, which is followed by step (4), then step (3), then step (5).

20. A process for the preparation of a pharmaceutical formulation comprising Dronedarone, or a salt thereof, which process comprises a process for the preparation of Dronedarone, or, a salt thereof, as claimed in claim 18, followed by bringing into association Dronedarone (or a salt thereof) so formed, with (a) pharmaceutically-acceptable excipient(s), adjuvant(s), diluent(s) or carrier(s).

21. A process for the preparation of a pharmaceutical formulation comprising Dronedarone, or a salt thereof, which process comprises a process for the preparation of Dronedarone, or, a salt thereof, as claimed in claim 18, followed by bringing into association Dronedarone (or a salt thereof), with a pharmaceutically acceptable non-ionic hydrophilic surfactant selected from poloxamers, and, optionally, one or more pharmaceutical excipients.

22. A process for the preparation of an intermediate of Dronedarone, or a salt thereof, which process comprises a process step as claimed in claim 1, followed by any one or more of the following process steps (2), (3) and (4)
   2) in the case of 2-butyl-3-(4-methoxybenzoyl)-5-nitrobenzofuran), converting the 4-methoxy moiety to a 4-hydroxy moiety; followed by, in any feasible order,
   3) converting a nitro ($-NO_2$) group to a methylsulfonylamino ($-NHS(O)_2CH_3$) group; and
   4) converting an $-OH$ group to a $-O-(CH_2)_3-N(C_4H_9)_2$ group.

23. A process as claimed in claim 2, wherein
$R^1$, $R^3$ and $R^4$ represent hydrogen;
X represents n-butyl; and
Z represents phenyl substituted in the para-position by $-OH$, $-OCH_3$ or $-O$-benzyl.

* * * * *

UNITED STATES PATENT AND TRADEMARK OFFICE
CERTIFICATE OF CORRECTION

PATENT NO. : 8,519,165 B2  
APPLICATION NO. : 12/681299  
DATED : August 27, 2013  
INVENTOR(S) : Lars Eklund Page 1 of 1

It is certified that error appears in the above-identified patent and that said Letters Patent is hereby corrected as shown below:

On Title Page 2, under References Cited, Other Publications:
Please replace "cation Claims intended for grant EP 08806486" with --Claims intended for grant EP 08806486--

Signed and Sealed this
First Day of September, 2015

Michelle K. Lee
*Director of the United States Patent and Trademark Office*

UNITED STATES PATENT AND TRADEMARK OFFICE
CERTIFICATE OF CORRECTION

PATENT NO. : 8,519,165 B2  
APPLICATION NO. : 12/681299  
DATED : August 27, 2013  
INVENTOR(S) : Lars Eklund Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 368 days.

Signed and Sealed this
Fifteenth Day of September, 2015

Michelle K. Lee
*Director of the United States Patent and Trademark Office*